(12) United States Patent
Henniges

(10) Patent No.: US 11,419,973 B2
(45) Date of Patent: Aug. 23, 2022

(54) MEDICAL/SURGICAL LAVAGE UNIT WITH A PUMP THAT INCLUDES A BELLOWS CHAMBER AND A SUPPLEMENTAL CHAMBER

(71) Applicant: Stryker Corporation, Kalamazoo, MI (US)

(72) Inventor: Bruce Henniges, Galesburg, MI (US)

(73) Assignee: Stryker Corporation, Kalamazoo, MI (US)

( * ) Notice: Subject to any disclaimer, the term of this patent is extended or adjusted under 35 U.S.C. 154(b) by 761 days.

(21) Appl. No.: 16/257,435

(22) Filed: Jan. 25, 2019

(65) Prior Publication Data

US 2019/0151531 A1 May 23, 2019

Related U.S. Application Data

(63) Continuation of application No. 14/850,240, filed on Sep. 10, 2015, now abandoned, which is a
(Continued)

(51) Int. Cl.
*A61M 3/02* (2006.01)
*A61M 1/00* (2006.01)

(52) U.S. Cl.
CPC ......... *A61M 3/0258* (2013.01); *A61M 1/0058* (2013.01); *A61M 3/022* (2014.02); *A61M 3/0208* (2014.02); *A61M 3/0283* (2013.01)

(58) Field of Classification Search
CPC .............. A61M 1/0064; A61M 1/0058; A61M 3/0258; A61M 3/0208; A61M 3/0283
See application file for complete search history.

(56) References Cited

U.S. PATENT DOCUMENTS

| | | | |
|---|---|---|---|
| 4,617,915 A | 10/1986 | Arakawa | |
| 5,046,486 A | 9/1991 | Grulke et al. | |
| 5,147,281 A * | 9/1992 | Thornton | A61M 60/148 600/16 |

(Continued)

FOREIGN PATENT DOCUMENTS

| | | |
|---|---|---|
| GB | 1352843 A | 5/1974 |
| JP | S 60-95179 | 6/1985 |

(Continued)

OTHER PUBLICATIONS

English language abstract for JP 2013-502258 extracted from espacenet.com database on Mar. 11, 2019, 1 page.
(Continued)

*Primary Examiner* — Tiffany Legette
(74) *Attorney, Agent, or Firm* — Howard & Howard Attorneys PLLC

(57) ABSTRACT

A lavage unit may include a handpiece configured to house a pump to which an irrigation tube is connected. The pump may include a bellows defining a pump chamber. When the bellows is reciprocated by a linkage, the bellows draws irrigation fluid from the irrigation tube into the pump chamber and then discharges the fluid out of the pump chamber through an outlet. The pump further includes a section formed from compressible or flexible material that defines a supplemental chamber. The linkage is connected to said pump to alternatively compress the bellows forming the pump chamber and the material forming the supplemental chamber. During the movement of the linkage a valve located between the pump chamber and the supplemental chamber reciprocates with the linkage.

19 Claims, 16 Drawing Sheets

Related U.S. Application Data continuation of application No. PCT/US2013/031350, filed on Mar. 14, 2013.

(56) References Cited

U.S. PATENT DOCUMENTS

| | | | |
|---|---|---|---|
| 5,746,721 A | 5/1998 | Pasch et al. | |
| 6,022,329 A * | 2/2000 | Arnett | A61M 3/022 601/155 |
| 6,059,754 A | 5/2000 | Pasch et al. | |
| 7,153,287 B2 | 12/2006 | Henniges et al. | |
| 9,987,403 B2 | 6/2018 | Kidman et al. | |
| 2008/0033348 A1 | 2/2008 | Bidoia | |
| 2010/0262073 A1 * | 10/2010 | Henniges | A61M 1/774 604/82 |

FOREIGN PATENT DOCUMENTS

| | | |
|---|---|---|
| JP | S6095179 U | 6/1985 |
| JP | H 02-230977 | 9/1990 |
| JP | H02230977 A | 9/1990 |
| JP | 2013-502258 | 1/2013 |
| JP | 2013502258 A | 1/2013 |
| WO | 9625188 A1 | 8/1996 |
| WO | 99017661 A1 | 4/1999 |
| WO | 2006040273 A1 | 4/2006 |
| WO | 2011021028 A1 | 2/2011 |

OTHER PUBLICATIONS

English language abstract for JPH 02-230977 extracted from espacenet.com database on Mar. 11, 2019, 2 pages.
Machine-assisted English translation for JPS 60-95179 extracted from espacenet.com database on Dec. 6, 2018, 2 pages.
Partial International Search Report for Application No. PCT/US2013/031350 dated Oct. 14, 2013, 2 pages.
PCT "International Search Report and Written Opinion" for PCT/US2013/031350, dated Feb. 2014.

* cited by examiner

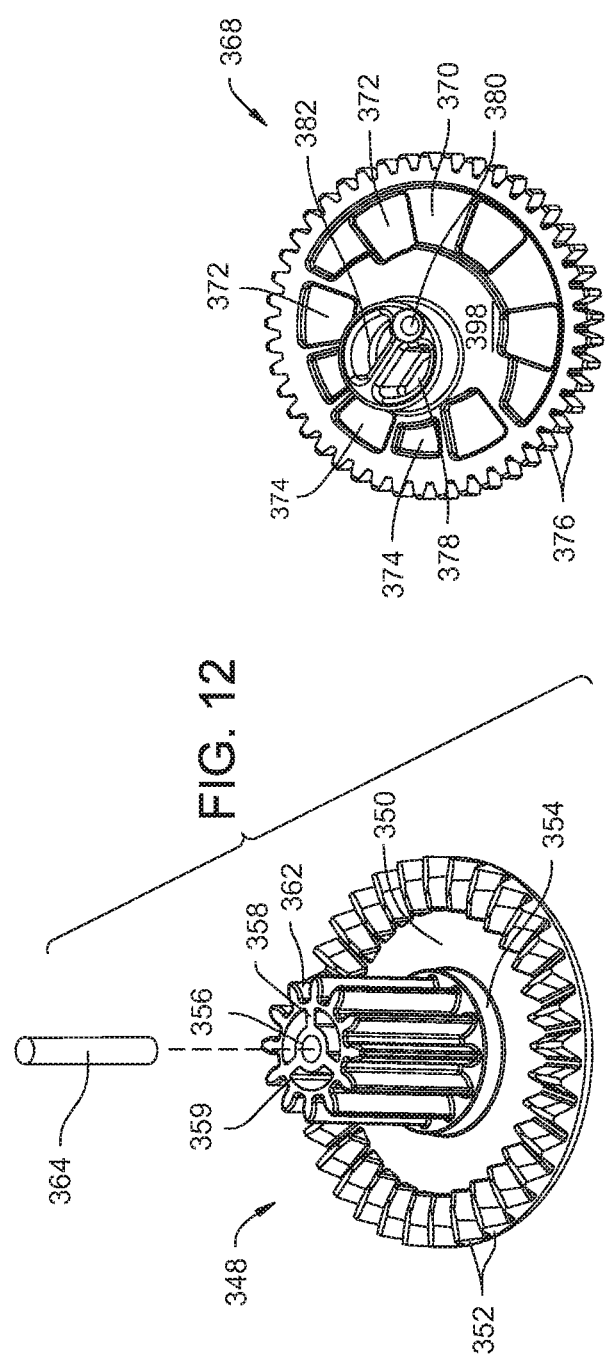

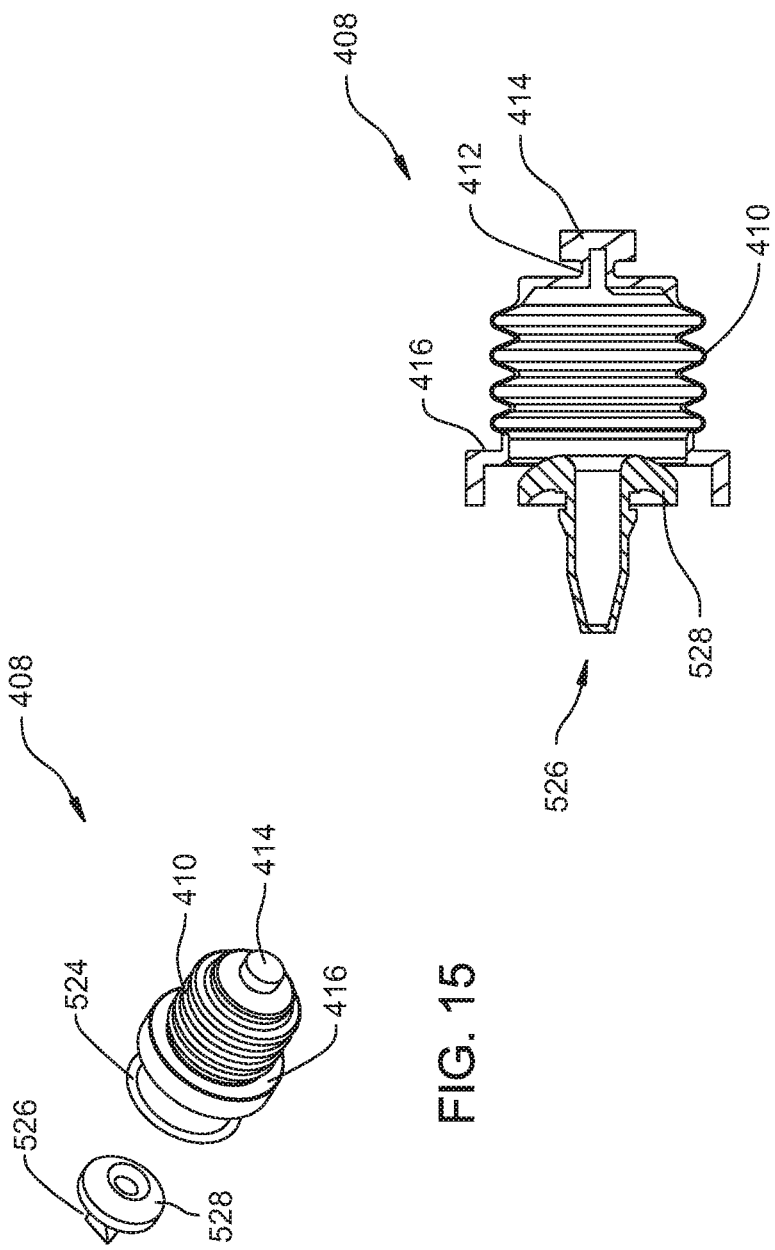

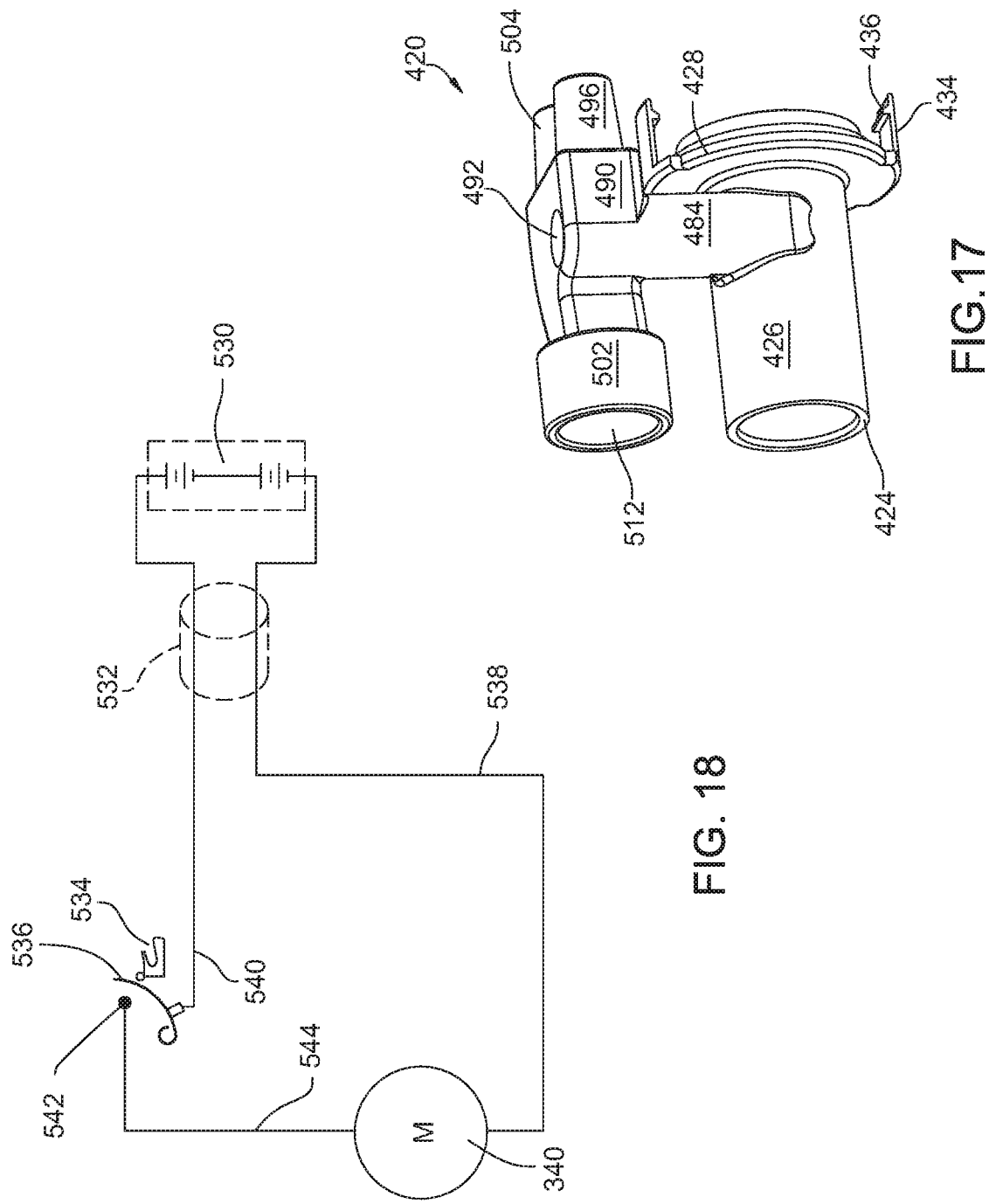

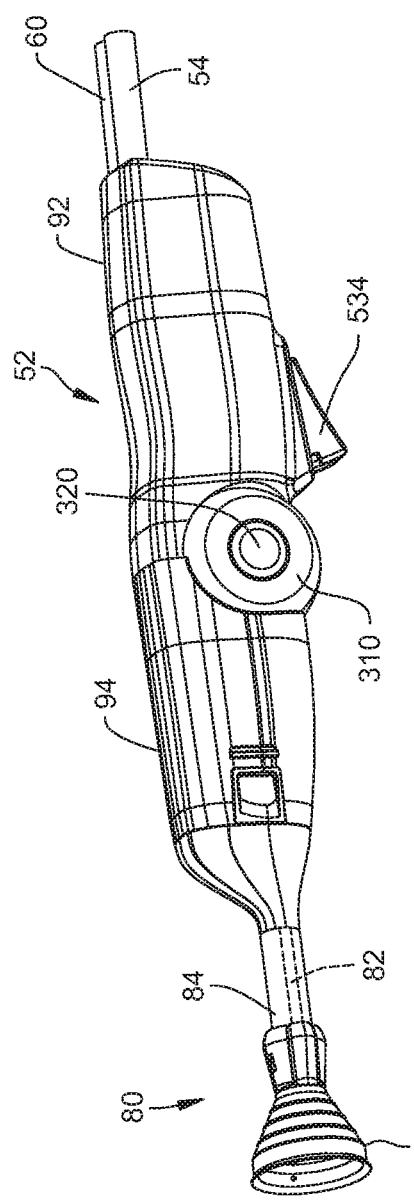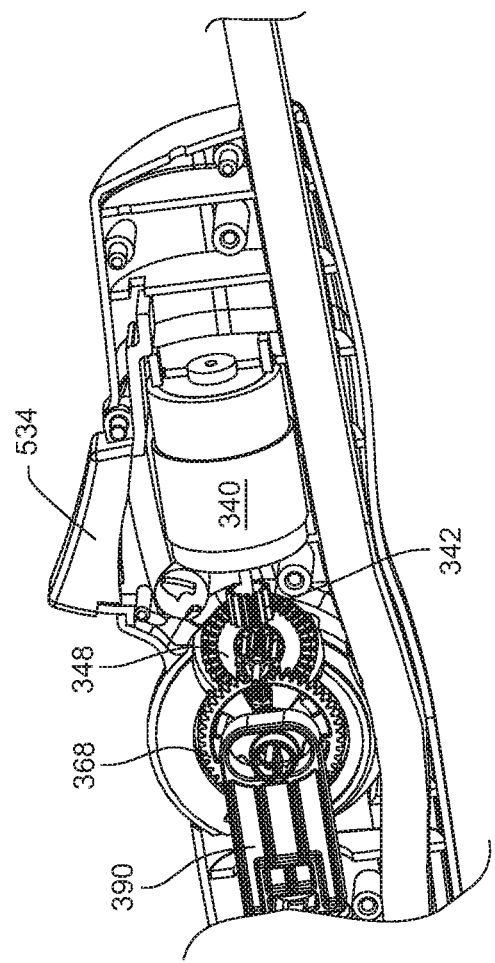

MEDICAL/SURGICAL LAVAGE UNIT WITH A PUMP THAT INCLUDES A BELLOWS CHAMBER AND A SUPPLEMENTAL CHAMBER

RELATED APPLICATIONS

This application is a continuation of and claims priority to and the benefit of U.S. application Ser. No. 14/850,240 (U.S. Publ. No. 2016/0067401), filed on Sep. 10, 2015, which is a continuation of PCT App. No. PCT/US2013/031350, filed on Mar. 14, 2013, all of which are hereby incorporated herein by reference in their entirety.

BACKGROUND

In many surgical and medical procedures, a lavage unit is employed to deliver fluid to a particular location on or in the body of a person receiving medical attention. For example, during orthopedic surgery, a lavage unit may be employed to deliver pressurized pulses of water or saline solution to an exposed surface of the bone in order to clean the bone. There are also some non-surgical procedures performed which likewise make it desirable to apply pulses of water to a specific site on an individual's skin. Thus, if an individual is suffering from some type of bed sore or some other type of skin wound, it is a common practice to use a lavage unit to clean the wound prior to applying a dressing to the wound.

A common type of medical/surgical lavage unit includes a handpiece to which a tip assembly is selectively attached. Often, inside the handpiece is a small pump that periodically delivers a quantity of pressurized fluid. Alternatively, the pressurized fluid is delivered to the handpiece from an external pump. The fluid is discharged through a discharge tube integral with the tip assembly to the selected site on or in the patient. These lavage units deliver fluid in pressurized pulses for two reasons. One reason is that fluid pulses quickly strike the site to which they are applied and leave the site; this action fosters the desirable removal of debris from the site. Secondly, the discrete fluid pulses do not obstruct the view of the site as much as it can be obstructed when exposed to a continuous flow of pressurized fluid.

Most lavage units, in addition to having a conduit through which the sterile fluid is discharged, have a conduit through which the discharged fluid and entrained debris is removed from the site to which it is applied. Typically, the fluid is initially withdrawn from the site through a suction tube, also part of the tip assembly. The fluid, as well as any debris in the fluid stream, then flow through a conduit integral with the handpiece. The handpiece suction conduit is connected to a second suction tube that is connected to a suction system separate from the irrigator. Thus, given their ability to essentially simultaneously clean a site on a patient and remove the debris generated by the cleaning process, it should be readily apparent why irrigators have become useful tools for facilitating many medical and surgical procedures.

Applicant's U.S. Pat. Nos. 6,022,329 and 7,153,287, and its U.S. Provisional Patent Application No. 61/733,989 filed 6 Dec. 2012, each of which is explicitly incorporated herein by reference, disclose use-once lavage units. In these documents and in other publications, lavage units are sometimes referred to as irrigators.

During a procedure, the practitioner using the lavage unit may want to apply the unit to different sections of the patient's tissue. Often these tissue sections are in different orientations and heights relative to the ground plane. For example, at one point in the procedure it may be desirable to hold the lavage unit against tissue that is generally vertically oriented. At another time during the same procedure, it may be desirable to hold the lavage unit against tissue that is generally horizontal, parallel to the ground plane. A disadvantage of a number of current lavage units is that they are not ergonomically designed to be held in the different orientations in which they may be used.

A number of irrigators are formed with bellows pumps. The bellows of this pump is reciprocated to first draw fluid into the pump chamber defined by the bellows and then force the fluid out of the chamber. An irrigator with a bellows pump is often designed so that the flow into the bellows is along a path that includes two U-shaped turns. The fluid flowing through a lavage unit that includes conduits with these turns inevitably undergoes some pressure drop as a result of having flow through this circuitous flow path. This pressure drop reduces the efficiency of the actual discharge of fluid from the irrigator. Further, to supply the fluid to the bellows it is necessary to provide the lavage unit with conduits that are formed with these numerous curves. Having to provide conduits with these shapes can contribute to the complexity of design, the size and cost of providing the lavage unit.

SUMMARY

This invention relates generally to a new and useful lavage unit. The lavage unit of this invention is designed to be ergonomically held in a number of different orientations against the tissue to which the unit is applied.

The lavage unit of this invention includes a handpiece and a tip assembly. The handpiece consists of a handgrip and a barrel. Internal to the handpiece is a pump. A motor, also internal to the handpiece, is connected to and powers the pump. The handpiece of this invention is further constructed so that that barrel is pivotally attached to the handgrip. Thus the barrel can be positioned relative to the handgrip so that the barrel is generally axially aligned with the handgrip. The barrel can further be positioned to project essentially perpendicularly from the handgrip.

In many versions of the invention, the lavage unit is further designed so that motor is disposed in the handgrip portion of the handpiece. The pump is disposed in the barrel. Often a gear that transfers the rotational motion output by the motor to the pump is mounted to the handpiece to rotate around the axis around which the barrel pivots.

It is a further feature of many lavage units of this invention that the tube through which irrigation fluid is supplied to the pump and the line through which suction is drawn are attached to the handpiece to be located around the outside of the arc around which the barrel pivots.

Some irrigators of this invention further include a pump with bellows with two tandem chambers. Irrigators having this feature are thus constructed so the inlet line opening into this bellows is essentially located at the distal end of the bellows. The outlet opening is located at the proximal end. Irrigators including this bellows are thus designed so that the inlet flow into the bellows is essentially along a linear path of travel. Irrigators constructed with this feature undergo less of a pressure drop as opposed to fluid that flows through irrigators wherein, prior to the fluid entering the bellows, the fluid transits a U-shaped path of travel.

BRIEF DESCRIPTION OF THE DRAWINGS

The invention is pointed out with particularity in the claims. The above and further features and advantages of this invention are understood from the following Detailed Description taken in conjunction with the accompanying drawings in which

FIG. 12 is a perspective view of the face gear internal to the handpiece;

FIG. 13 is a perspective view of the eccentric gear internal to the handpiece;

FIG. 15 is an exploded view of the valve and bellows internal of the pump;

FIG. 16 is a cross sectional view of the yoke and the bellows of the pump;

FIG. 17 is a perspective view of the pump housing internal to the handpiece;

FIG. 18 depicts the conductive components internal to the handpiece;

FIG. 19 is a perspective view depicting the handpiece when the barrel and handgrip are arranged so the barrel is longitudinally aligned with the handgrip;

FIG. 20 depicts the components internal to the around the joint between the barrel and handgrip when the barrel and handgrip are longitudinally aligned;

DETAILED DESCRIPTION

I. Basic Lavage Unit

Figure 1:
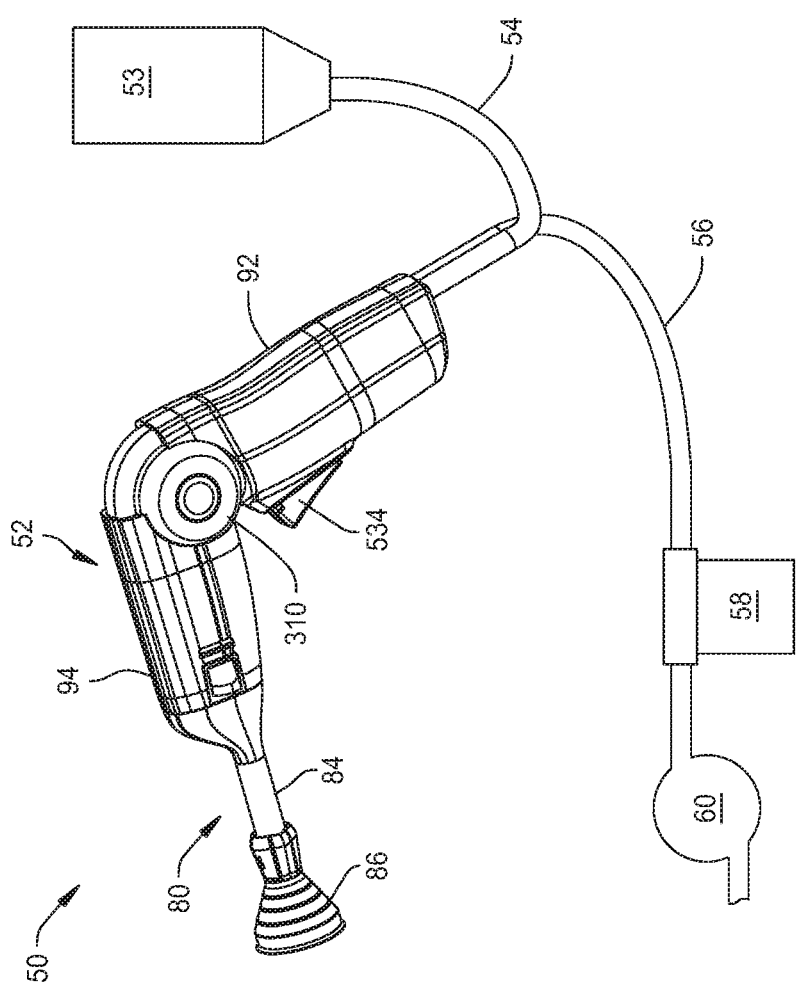
FIG. 1 is a perspective view of a lavage unit of this invention.
Figure 2:
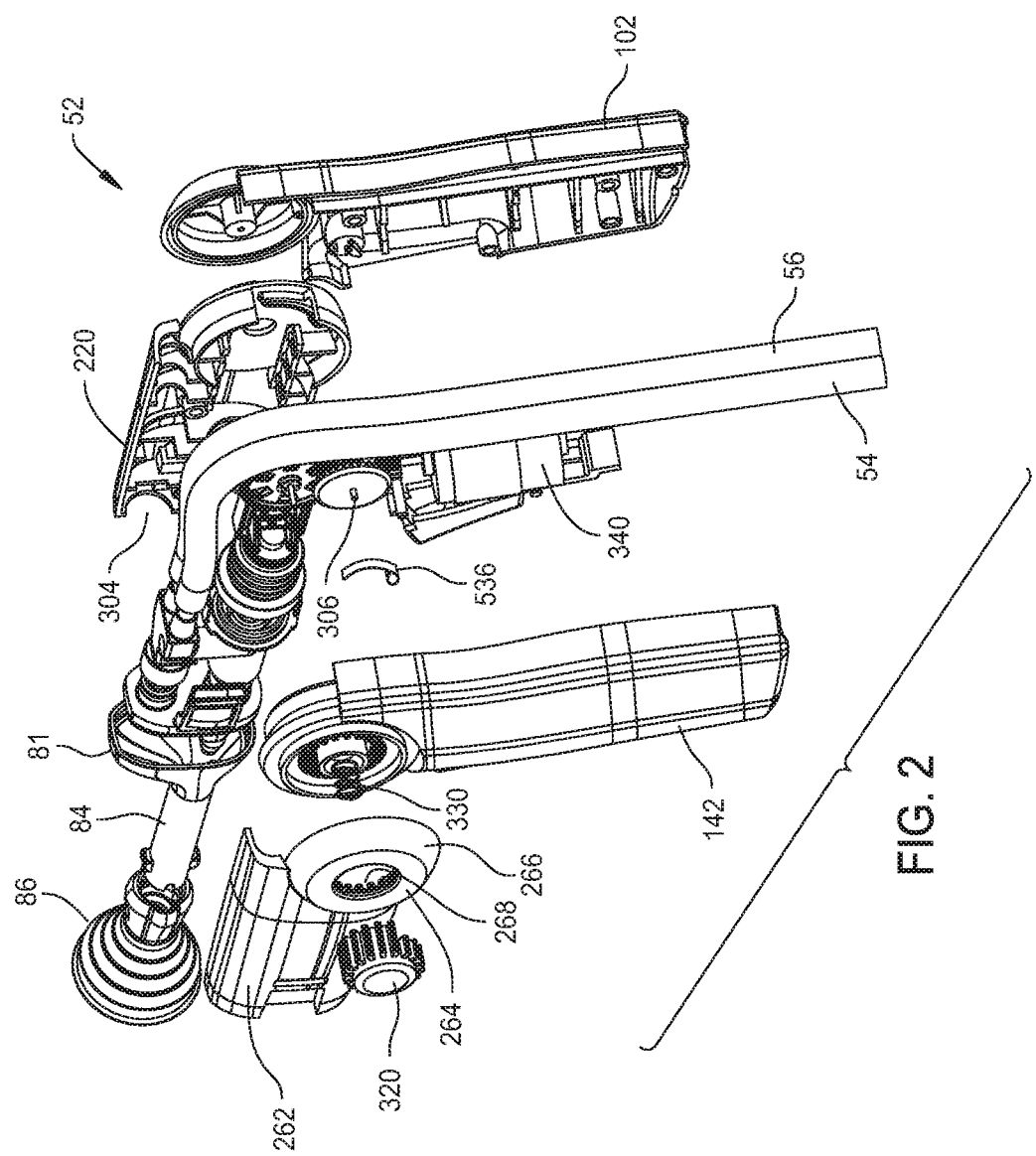
FIG. 2 is an exploded perspective view of the lavage unit.
Figure 3:
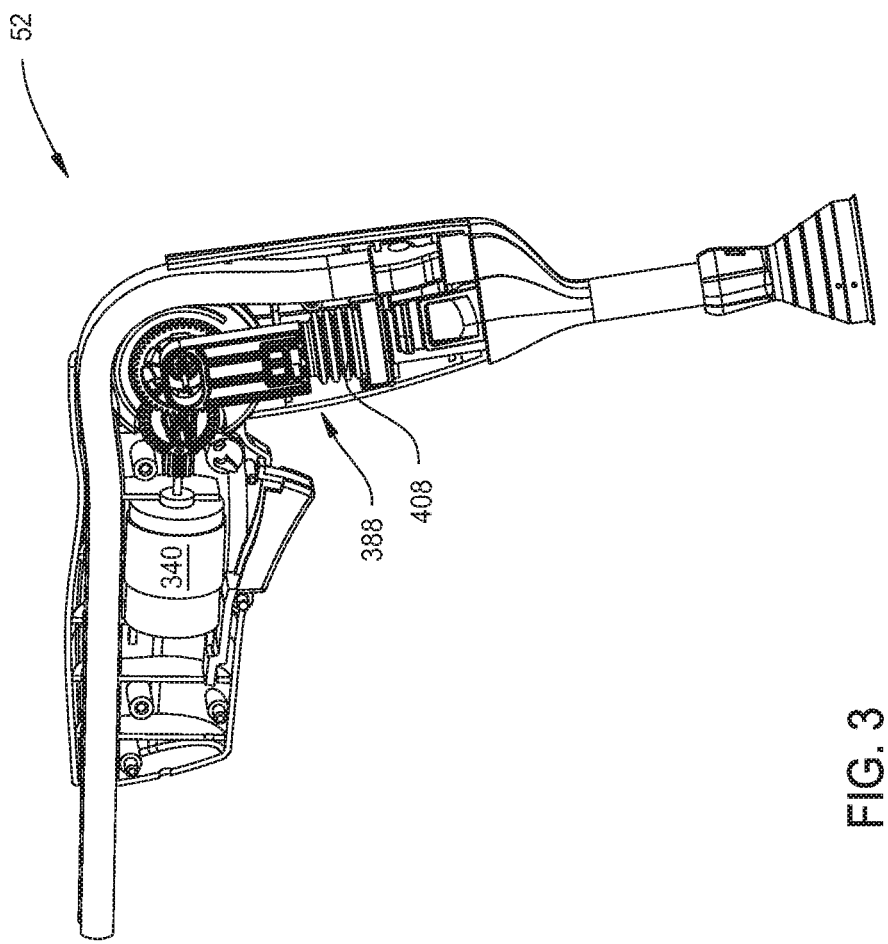
FIG. 3 is a plan view of the lavage unit with two of the handpiece shells removed to show the arrangement of the components internal to the handpiece.

FIGS. 1-3 depict the basic components of a lavage unit 50 of this invention. Lavage unit 50 includes a handpiece 52, sometimes called a body, to which a tip assembly 80 is removably attached. An irrigation tube 54 runs from a source of irrigating fluid 53 to the handpiece 52. A suction tube 56 is fitted to the handpiece 52. Suction tube 56 extends proximally to both a waste collection container 58 and a suction source 60. (Here "proximally" means towards the practitioner holding handpiece 52, away from the patient to which the tip assembly 80 is applied. "Distally" means away from the practitioner and towards the patient.) Internal to the handpiece 64 is a pump 388 to which the distal end of irrigation tube 54 is connected. Pump 388 is driven by a motor 340. The on/off state of the motor 340 is controlled by a trigger 534 that is pivotally mounted to the underside of the handpiece 64.

Tip assembly 80 includes a rigid irrigation tube 82. Irrigation tube 82, shown as dashed lines only in FIG. 19, that is disposed inside a suction tube 84. A spray shield 86 is removably disposed over suction tube 84. When the tip assembly 80 is attached to the handpiece 52, a first fluid communication path is established between an outlet port of pump 388 and irrigation tube 82. A second fluid communication path is established between the proximal end of suction tube 84 and suction tube 56 that is attached to and extends from the handpiece 52. The structure of the tip assembly 80 is not part of the present invention.

Handpiece 52 includes a proximally located handgrip 92. A barrel 94 is pivotally mounted to and extends distally forward from the handgrip 92. A lock button 320 holds the barrel 94 in the orientation relative to the handgrip 92 that is desired by the person using the lavage unit 50. Motor 340 is mounted in the handgrip 92. The pump 388 is located in the barrel. Gears 348 and 368 are also disposed in the handpiece 52. The gears 348 and 368 transfer the mechanical energy output by the motor into motion that reciprocates the pump. Tip assembly 80 is removably mounted to the distal end of the barrel. Irrigation tube 54 and suction tube 56 both extend longitudinally through at least a portion of both the handgrip 92 and the barrel.

Figure 4:
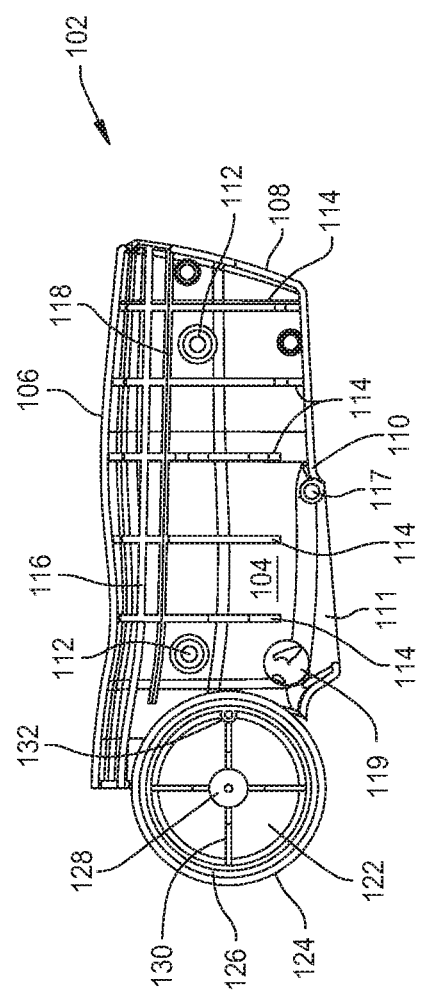
FIG. 4 is a plan view of the inside of handgrip right side shell.
Figure 5:
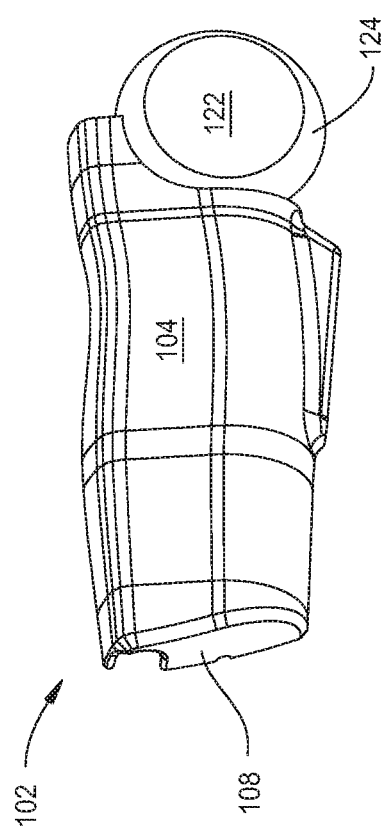
FIG. 5 is a perspective view of the outside of the handgrip right side shell.

Handgrip 92 includes right and left shells 102 and 142, respectively. Both shells 102 and 162 are single piece components formed from a plastic such as a ABS or high impact polystyrene. As seen best in FIGS. 4 and 5, right shell 102 includes a base 104. A top rim 106 curves upwardly from the top edge of base 104. A proximal rim 108 curves upwardly from the proximal end of the base 104. A bottom rim 110 curves upwardly from a bottom edge of the base 104. It should be understood that proximal rim 108 extends between top and bottom rims 106 and 110, respectively. A number of posts 112 project outwardly from the inner face of the base 102. Each post 112 is formed with a closed end bore (not identified) that extend inwardly from the end of the post.

Webs 114, 116 and 118 extend outwardly from the inner face of the base 104. Webs 114 are the vertically extending webs in that they also extend downwardly from top rim 106. The two most proximal webs 114 extend to bottom rim 110. Webs 116 and 118 are horizontally extending in that they generally extend perpendicularly away from shell proximal rim 108. Both webs 116 and 118 are located relatively close to top rim 106, with web 116 being closer to the rim 106. Both webs 116 and 118 intersect the webs 114. Web 118 extends outwardly beyond web 116. Webs 114, 116 and 118 provide some structural rigidity to the right shell 102. Some of the webs 114 are further shaped to serve as the support members against which motor 340 is seated. Webs 114, 116 and 118 are further shaped to serve as the serve as the support structure internal to the handgrip 92 against which the tandem assembly of irrigation tube 54 and suction tube 56 is seated. Thus tubes seat against the upper surface of web 116.

Right shell 92 is further formed so that bottom rim 110 does not project up from whole of the bottom end of base 104. Rim 110 is formed to define a notch 111 in the shell 92. Notch 111 extends distally forward from a location approximately one-half the distance along base 104. The notch 111 terminates at a position approximately 1 cm proximal to the distal end of the base. A post 117 extends upwardly from the inner surface of the shell base 104 adjacent the proximal end of notch 111. A post 119 extends upwardly from the inner surface of shell base 104 from a position slightly above notch 111.

Integral with right shell 92 is an ear 122 that is generally circular in shape. Ear 122 is located forward of the shell base 102 and is spaced slightly outwardly of the base. A circular rim 124 extends outwardly from the inner face of and surrounds the ear 122. Rim 124 is tapered in that the inner and outer diameters of the rim increase with distance from the face of ear 122. The rim 124 is further formed so as to have groove 126 that extends inwardly from the face of the rim. Two bosses, bosses 128 and 132 extend upwardly from the inner face of ear 122. One boss, boss 128, extends upwardly from the center of ear 122. The second boss, boss 132, extends upwardly from a location adjacent the inner perimeter of rim 124. Boss 132 has an outer diameter less than the outer diameter of boss 128. Each boss 128 and 132 is formed with a closed end bore. Ear 122 is further formed to have four webs 130, only one of which is identified. Webs 130 extend radially outwardly from boss 128. Webs 130 are equiangularly spaced apart from each other. Three of the webs 130 extend to the inner surface of the rim 124. The fourth web 130 extends between boss 128 and boss 132.

The handgrip left shell 142 includes a base 144 that is essentially a mirror image of right shell base 104. Three rims 146, 148 and 150 extend outwardly from the perimeter of the inner surface of base 144. Rim 146 mates with right shell top rim 106. Rim 148 mates with right shell proximal rim 108. Rim 150 mates with right shell bottom rim 110. The left shell 142 is formed with posts 152 that are analogous to right shell posts 112. Each post 152 is formed with a pin 154 (one identified) that projects outwardly from the center of the post. The pins 152 have diameter that facilitate the press fitting of the pins in the bore internal to the right shell posts 112. Thus, when the lavage unit 30 is assembled, the seating of the left shell pins 154 in the right shell posts 112 holds the shells 92 and 142 together.

Handgrip left side shell 142 includes vertically extending webs 158, only one identified. Webs 158 are similar to and perform the same function as right side shell webs 114. The left side shell 142 also includes horizontally extending webs 160 and 162. Web 160 is analogues in location and shape to the right side shell web 116. Web 162 is analogues in location and shape to the right side shell web 118.

Handgrip left side shell 142 also has a post 155 and a post 157. Post 157 is essentially identical to right side shell post 117. Post 157 is essentially identical to right side shell post 119.

An ear 166 is integral with and extends forward from the left side shell base 144. Ear 166 is generally circular and, when shells 102 and 142 are placed together, coaxial with right side shell ear 122. In terms of side-to-side cross sectional thickness, ear 166 is wider than ear 122. On the inner face of the left side shell 142, ear 166 has a base surface 168 that is generally circular in shape. Base surface 168 is centered on the axis that runs side-to-side through the ear 166. A boss 170 protrudes outwardly from the center of the base surface 168. Boss 170 is formed with a closed end bore, (not identified) that is centered on the center axis of the ear. An arcuate rib 172 also protrudes outward from base surface 168. Rib 172 is concentric with and radially spaced outwardly from the boss 170. In the depicted version of the invention, rib 172 protrudes a greater distance above surface 168 than boss 170.

The left side shell ear 166 is further formed to have a rim 174 that extends around the base surface 168. Rim is located outwardly of the base and spaced radially outwardly from rib 172. A rib 176 extends outwardly from outer surface of rim 174. Rib 176 is concentric with rim 174 which is concentric with boss 170. The rib 176 is located around the upper portion of rim 174. Ear 166 also has a recessed surface 180 that relative to base surface 168 is located closer to the outer surface of the left side shell 142. Recessed surface is generally circular in shape and interrupts both base surface 168, rib 172 and rim 174. A boss 182 extends outwardly from the center of recessed surface 180. A closed end bore (not identified) extends inwardly from the center of boss 182. Recessed surface 180 and boss 182 are located such that when the shells 102 and 142 are placed together the axis around which the surface 180 and boss 182 are centered is coaxial with the axis of right side shell boss 132. A rib 184 also protrudes upwardly from recessed surface 180. Rib 184 is concentric with boss 182 and radially spaced away from the boss. Rib 184 is lower in height relative to the recessed surface 180 than boss 182.

From the outside, the left shell ear 166 is seen to have a generally circular base surface 188. Base surface 188 corresponds to the base surface 168 on the inner side of the ear 166. A boss 190 projects outwardly from base surface 188. A tube shaped sleeve 192 also projects outwardly from base surface 188. Sleeve 192 is radially spaced outwardly from and extends above boss 190. Left shell ear 166 is further seen to have step 194 that is located outward of base surface 188. Step 194 is present owing to the presence of recessed surface 180 on the inner side of the ear 166. Step 194 interrupts and arcuate section of base surface 188 and extends to the outer surface of sleeve 194. A circular inner ring surface 196 is located above and around base surface 188 and step 194. The inner perimeter of ring surface 196 is spaced radially away from sleeve 192. Ear 166 also has teeth 198 that extend inwardly from the inner perimeter of the ring surface 196. Teeth 198 project into the space above the ear base surface 188 and step 194.

The outer portion of ear 166 has an outer ring surface 204 that extends circumferentially around the inner ring surface 196. Outer ring surface 204 is located outward of the inner ring surface 196. A rim 202 is located between the inner and outer ring surfaces 196 and 204, respectively. Rim 202 extends outwardly of the outer ring surface 204.

Figure 6:
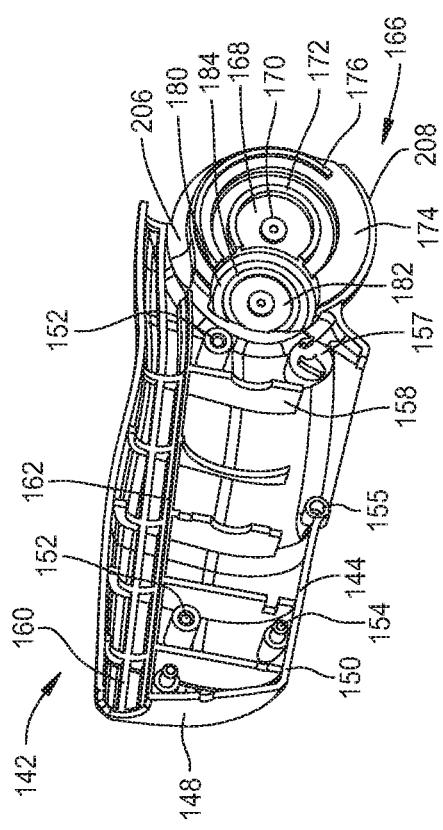
FIG. 6 is a perspective view of the inside of the left side shell.
Figure 7:
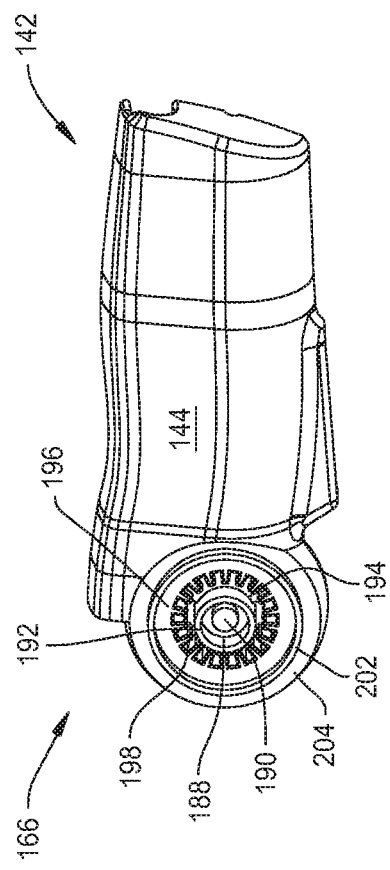
FIG. 7 is a perspective view of the outside of the handpiece left side shell.

The left shell ear 166 has a first side wall 206 that extends inwardly from outer surface 204. Side wall 206 extends distally from web 166 and curves around the distal front portion of ear 166. This side wall 206 has a profile that in a lateral cross section appears concave. Side wall 206 terminates in a second curving side wall, wall 208. In FIG. 6, only the edge of side wall 206 is identified. Wall 208 curves around the lower portion of the ear. Wall 208 has a shape in cross section that is either linear or convex.

Figure 8:
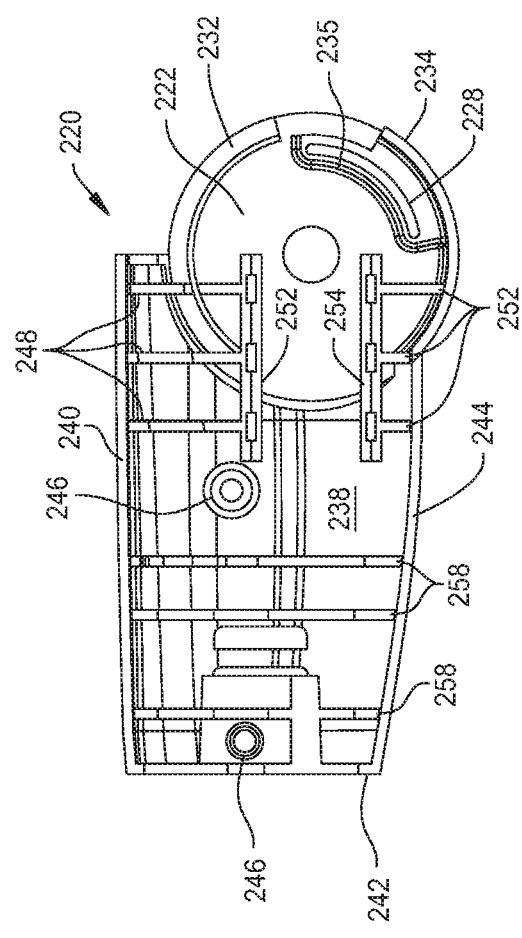
FIG. 8 is a plan view of the inside of the barrel right side shell.
Figure 9:
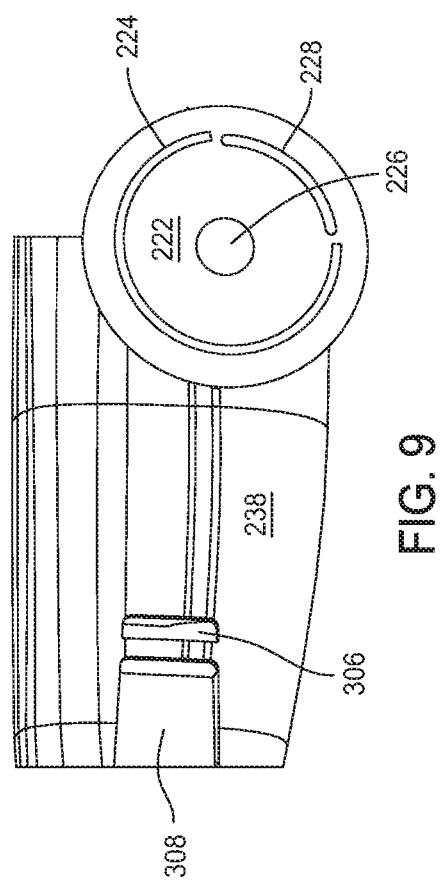
FIG. 9 depicts the outside of the barrel right side shell.

The handpiece barrel 92 includes right and left side shells 220 and 262, respectively. The right side shell 220, now described by reference to FIGS. 8 and 9 includes a foot 222 that is generally arcuate in shape. More particularly, foot 222 has a diameter along its outer surface equal to the diameter of rim 124 integral with the handgrip right side shell ear 122. The outer surface of foot 222 is generally planar. An arcuately shaped rib 224 protrudes outwardly from the outer surface of foot 222. Rib 224 is located inwardly from the outer perimeter of foot 222. The rib 224 is positioned so that when the handpiece 30 is assembled, the rib 224 seats in and moves within groove 126 formed in rim 124. Foot 222 is formed with a center located opening 226. The foot 222 also has an arcuately shaped slot 228. Slot 228 is located proximal to and below opening 228. The slot 228 is positioned so that when the handpiece is assembled, the boss 132 integral with the handgrip right side shell ear will be in registration with the slot.

Two skirts extend inwardly from the inner surface of foot 222. Both skirts extend from the outer perimeter of the foot. A first skirt, skirt, 232 extends inwardly from the top of the foot 222. In lateral cross section, skirt 232 has a convex profile similar to the profile of side wall 206 of handgrip left side ear 166. Skirt 234 extends inwardly from the bottom of the foot 222. Skirt 234 has the same cross sectional shape as wall 208 integral with handgrip left side ear 166. At the proximal end of foot 222 the skirts are spaced apart from each other to define a gap (not identified) between the skirts. When the handpiece is assembled the inner face of skirt 232 is flush with the portion of ear 166 that defines wall 206; the inner face of skirt 234 is flush with the portion of ear 166 that defines wall 208.

A rib 235 extends inwardly from the inner surface of foot 222. Rib 235 extends upwardly from an inside surface of skirt 234. Rib 235 curves around the perimeter of slot 228 closest to opening 226. The rib 235 curves towards the gap between skirts 232 and 234. Rib 235 does not extend upwardly from the inner surface of the foot 222 the same distance skirts 232 and 234 extend upwardly from the foot.

Forward of foot 222 shell 220 has a base 238. Base 238 has an outer surface that is located outwardly of the outer surface of foot 220. Three rims protrude outwardly from the outer perimeter of base 238 so as to project away from the inner surface of the base. A top rim 240 extends along the top of the outer perimeter of the base. At the proximal end of the base it will be noted that rim 240 is spaced away from skit 234. Thus there is a gap between the skirt 234 and the rim 240, (gap not identified). The distal end of rim 240 curves into a rim 242. Rim 242 extends upwardly from the distal end of the base 238. The rim 242 curves into a bottom rim 244. Bottom rim 244 extends outwardly from the bottom edge of the base 238. The bottom rim 244 extends proximally along base 238 and terminates at skirt 234.

Posts 246, similar to the posts 112, extend outwardly from the inner face of base 238. A number of webs extend vertically, top to bottom through shell 220. At the proximal portion of the shell three parallel webs 248 extend outwardly from the base and downwardly from top rim 240. The two proximalmost webs extend over the inner surface over foot 222. A web 252 is longitudinally aligned with each web 248. The two proximalmost webs 252 extend from skirt 234 and outwardly from the inner surface of foot 222. Each web 252 is spaced from the complementary web 248. Webs 248 extend downwardly from top rim 240 to a common web 250. Web 250 is perpendicular to the webs 248. Webs 252 extend upwardly from top rim 244 to a common web 254. Web 254 is perpendicular to the webs 252. Thus webs 250 and 254 are parallel to each. Each web 250 and 254 thus extends upwardly from the inner surface of foot 222 and the adjacent portion of base 238. Web 250 is located above opening 226. Web 254 is located below opening 226. While not identified, the facing portion of the webs 250 and 254 are formed with surfaces that are stepped inwardly from the highest portions of the webs.

Three additional vertically extending webs 258 extend upwardly from the inner surface of shell base 238. Webs 258 are parallel with and located forward of webs 248 and 252.

Each web 258 extends from the shell top rim 240 to the bottom rim 244. Webs 248 and 258 are formed with indentations (not identified) in which the suction tube 56 is seated. Webs 258 are further formed with indentations to receive the below described pump housing 420, (FIG. 17).

Figure 10:
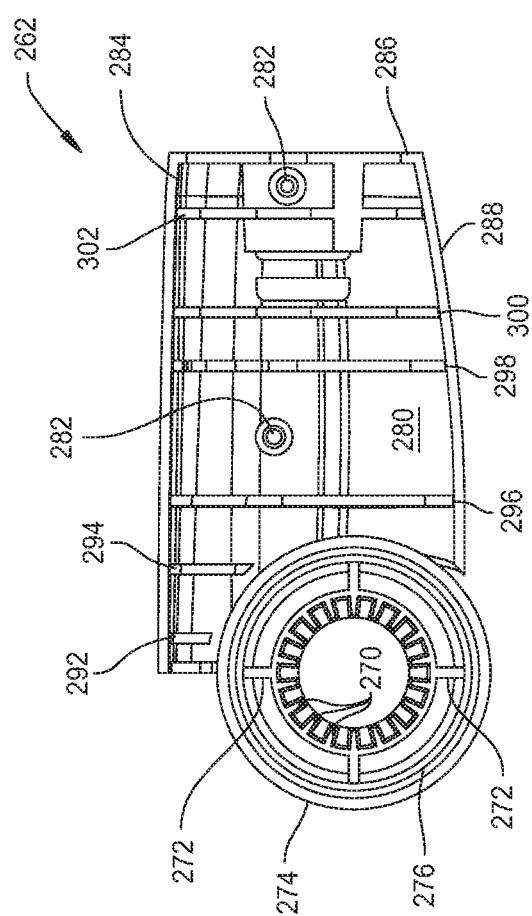
FIG. 10 is plan view of the inside of the barrel left side shell.

From FIGS. 2 and 10 it can be seen that the barrel left side shell 262 includes a flat, circular foot 264. A skirt 266 tapers outwardly and inwardly from foot 264. Skirt 266 is dimensioned so that the free end has an outer diameter equal to that of rim 174 of handgrip left side shell ear 166. Foot 264 also has a center opening 268.

Shell 262 is further formed so that teeth 270 extend upwardly from the inner surface of foot 264. Teeth 270 are arcuately spaced apart from each other and extend outwardly from the portion of the shell that defines opening 268. Four equiangular spaced apart webs 272, only two identified, extend outwardly from teeth 270. Webs 272 extend to a circular rim 274 that projects outwardly from foot 264. The rim 274 can also be considered to be the base surface of skirt 266. Rim 274 is formed with a circular groove 276 that extends inwardly from the face of the rim. When barrel shell 262 is positioned over handgrip shell 142, the rib 202 integral with handgrip shell 142 seats in barrel shell groove 276.

The barrel left side shell 262 has a base 280 that is located distally forward of foot 264. More particularly, base 280 is extends forward from skirt 266. Base 280 is thus located inward of the outer surface of foot 264. Posts 282 with pins (not identified) extend outwardly from the inner surface of base 280. Upon assembly of handpiece 52, the left shell posts 282 engage the right shell posts 246 so as to hold the shells 220 and 262 together. A top rim 284 extends outwardly from top perimeter of base 280. The shell 262 is shaped so the proximal end of the rim 284 is spaced from skirt 266. At the distal end of the base, the top rim 284 curves into a distal rim 286. The distal rim 286 curves into a bottom rim 288. The proximal end of the bottom rim 288 terminates a short distance, less than 0.5 cm, forward of skirt 266.

Six webs extend downwardly from the inner surface of top rim 284 and outwardly from the inner surface of shell base 280. The two most proximal webs, webs 292 and 294 extend toward and terminate a short distance before a section of skirt 266 that intersects the base 280. The remaining four webs, webs 296, 298, 300 and 302, extend to the bottom rim 288. Each of webs 292, 294, 296, 298, 300 and 302, is formed with one or more indentations (not identified) . These indentations facilitate the seating of either the irrigation tube 54 or the pump housing against the web 292, 294, 296, 298, 300 or 302.

The distal rims 242 and 286 of, respectively, shells 220 and 262 form the front end of the handpiece. The rims 242 are formed with notches 304, only one identified in FIG. 2. The notches 304 function as openings through which the tip assembly 80 is attached to the handpiece 50. Shell bases 238 and 184 are each provided with an opening 306 and an indentation 308, identified only in FIG. 9 for shell 220. Openings 306 and indentation 308 receive fastening components integral with the tip assembly 80. The method of removably attaching the tip assembly to handpiece 52 is not part of the present invention. Alternative features integral with the handpiece 52 and tip assembly may be used to facilitate this removable connection. Accordingly these features are only minimally discussed below.

When handpiece 52 is assembled, barrel right side shell foot 222 is located between the ears 122 and 166 of, respectively, handgrip shells 102 and 142. The handgrip left shell ear 166 is located between feet 222 and 264 of, respectively barrel shells 220 and 262. Collectively the handgrip ears 122 and 166 and the barrel feet 222 and 264 form a joint 310 between the handgrip 92 and the barrel 94. The barrel 94 is able to pivot around joint 310. This allows the angular orientation of the longitudinal axis of the barrel relative to the longitudinal axis of the handgrip 92 to be selectively set.

Figure 11:
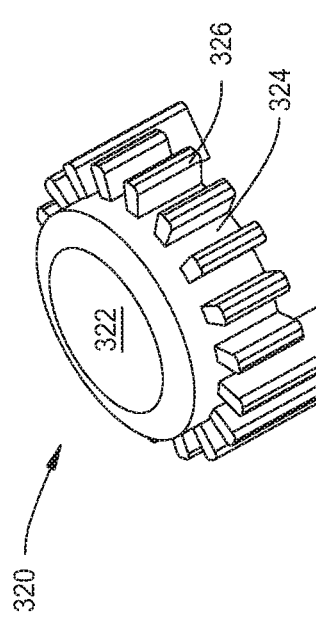
FIG. 11 is a perspective view of the handpiece lock button.

A lock button 320, now described by reference to FIGS. 2 and 11 holds the barrel 94 in the selective angular orientation relative to the handgrip 92. Button 320 includes a circular head 322. The center of the head 322 is recessed relative to the outer perimeter to facilitate the centering of the finger. A rim 324 extends circumferentially around the head 322. The components of handpiece 52 are formed so that the button head 322 and rim 324 can fit around the handgrip left shell sleeve 192 and within barrel left shell center opening 268. Arcuately spaced apart teeth 326 extend radially outwardly from rim 324. The teeth 326 are located below button head 322. The teeth 326 are spaced apart from each other so as to be able to engage both the handgrip left shell teeth 198 and the barrel left shell teeth 270. Around an arcuate section of the button 320, a set of teeth 326 are shorter than the other teeth 326. When the button is fitted over the handgrip left shell ear 166, the short teeth 326 are disposed over step 194.

A spring 330, seen only in FIG. 2, is disposed between handgrip left shell ear boss 190 and sleeve 192. Spring 330 presses against the inner surface of button head 322. The spring 330 thus places a biasing force on the button 320 the results in the displacement of the button so that button teeth 326 are normally seated between barrel teeth 270. The outward movement of the button is blocked by the abutment of the button teeth 326 against the inner surface of the barrel left side shell foot 264.

Button teeth 326 always are engaged with the handgrip left side shell teeth 198. The engagement of the button teeth 326 with the barrel teeth 270 thus holds the barrel 54 in a fixed angular orientation relative to the handgrip 52. The button is in the locked position. To adjust the angular orientation of the barrel, button 320 is depressed. The manual force of a finger against the button 320 is enough to overcome the force of spring 330. The inward displacement of the button 320 moves the button teeth 326 out of engagement with the barrel teeth 270. When the button 320 is so disengaged, the button can be considered in the barrel adjust state. The angular orientation of the barrel 54 can then be adjusted. The release of the finger force against the button causes spring 330 to return the button to the locked position.

Motor 340 is disposed between handgrip shells 102 and 142. More particularly, the motor is supported in the handgrip 92 between right side shell webs 114 and right side shell webs 158. A rotating shaft, not identified, extends forward from the body of the motor 340. A gear 344, identified only in FIG. 30 is fitted to the free end of the shaft to rotate with the shaft. When the motor 340 is seated in handgrip 92, gear 344 is disposed in the handgrip left side shell ear 166 and barrel right side shell foot 222.

Gear 344 engages a face gear 348 also internal to the handgrip 92. The face gear 348, as seen in FIG. 12, includes a disc shaped base 350. Teeth 352 extend upwardly from the base 350 so as to extend around the outer perimeter of the base. A raised circular pedestal 354 extends upwardly from the center of base 350. Inner and outer sleeves 356 and 359, respectively, extend upwardly from the exposed surface of pedestal 378. Pedestal 354 and sleeves 356 and 359 are coaxial with the center axis, the rotational axis of gear base 350. The inner surface of outer sleeve 359 is spaced radially outwardly away the inner sleeve 380. Arcuately spaced apart webs 358 extend between the outer surface of the inner sleeve 356 to the adjacent inner surface of the outer sleeve 384. Not identified is the coaxial through bore that extends through the inner sleeve 356 and the underlying pedestal 354. Outer sleeve 359 is formed with gear teeth 362.

Face gear 348 is positioned so that the toothless side of base 350 is disposed against left side shell boss 182. A pin 364, identified only in FIG. 12, rotatably holds the face gear 348 to the handgrip 92. Pin 364 extends through the axial bore through pedestal 354 and inner sleeve 356. One end of pin 364 is seated in the bore integral with right side shell boss 132. The opposed end of pin 364 is seated in the bore integral with left side shell boss 182. The face gear 348 is positioned so the gear base 350 is adjacent left shell boss 182. When handpiece 64 is assembled, gear 344 engages face gear teeth 352.

The face gear 348 drives an eccentric gear 368 also rotatably disposed in the handgrip 92. The eccentric gear 368, seen best in FIG. 13, is formed with a circular base 370. The base 370 is formed with a number of arcuately spaced apart through openings 372. Base 370 is also formed to have a number of arcuately spaced apart recesses 374. The recesses 374 are located inwardly of the outer perimeter of the base. In the depicted version of the invention, the recesses subtend different arcs. Further, the recess 374 that extends the large arc intersects plural openings 372. Teeth 376 protrude outwardly from the outer perimeter of base 370. A cylindrical head 378 protrudes upwardly from gear base 370. The center longitudinal axis of the head 378 is laterally offset from the rotation axis of the base 370. The eccentric gear is further formed to have a through bore 380. Bore 380 extends through the center of the base 370 and an outer portion of head 378 that extends over the rotational axis of the base 398. The bore 380 is thus centered on the axis around which eccentric gear 368 rotates. Gear 368 is formed with two voids 382. Voids 382 extend through the head 378 and the portion of the base 398 below the head. Voids 382 are symmetric around a plane that bisects bore 380.

A pin 386, identified in FIG. 2, rotatably holds the eccentric gear 368 to the handgrip 92. One end of pin 386 is seated in the bore integral with right side shell boss 128. The opposed end of pin 386 seats in bore integral with left side shell boss 170. It should thus be appreciated that gear 368 is mounted to the handpiece 52 to rotate around the axis around which barrel 94 rotates relative to handgrip 92. When the handpiece 52 is assembled, eccentric gear teeth 376 engage teeth 362 of the face gear 348.

Figure 14:
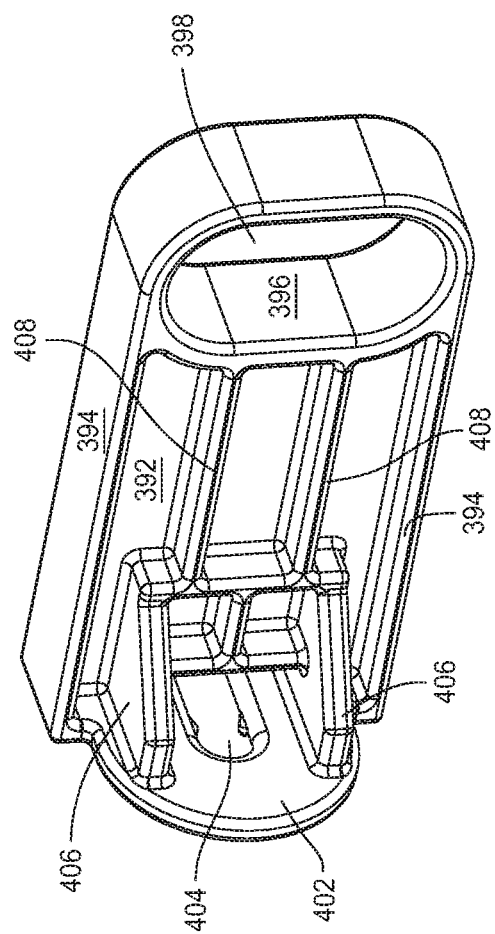
FIG. 14 is a perspective view of the yoke of the pump.

Eccentric gear 368 reciprocates a yoke 390 that disposed in handpiece joint 310. The yoke 390, as seen in FIG. 14, is part of pump 388, is a single piece component that includes a generally rectangular plate 392. Yoke 390 is orientated so the longitudinal axis of the yoke is parallel to the longitudinal axis through the barrel 94. The overall width of the yoke is such that the yoke can seat on and slide between webs 250 and 254 integral with the barrel left side shell 220. Two beams 394 extend outwardly from the side edges of the plate 392 and extend rearwardly beyond the proximal end of the plate 392. Beams 394 curve inwardly towards each other and meet at a location spaced rearward from the proximal end of the plate. Beams 394, as well as a beam 396, define an oval opening 398. The major axis of opening 398 is perpendicular to the longitudinal axis of plate 392. Opening 398 has a minor axis with a width dimensioned to receive eccentric gear head 378.

Yoke 390 is further formed so a tab 402 extends perpendicularly outwardly from plate 392 at the distal end of the frame. Tab 402 is formed with a U-shaped slot 404 the open end of which is located adjacent the end of the frame directed to the base 238 of the barrel right side shell 220. Brackets 406 extend from the proximally directed face of tab 402 to the surface of the plate 392. Additional beams 408, only two of which are identified, also project upwardly from the surface of the plate.

Upon assembly of the handpiece 52, the yoke 390 is seated on the inner stepped portion of webs 250 and 254. Eccentric gear head 378 is disposed in yoke opening 398.

Yoke 390 drives a bellows 408, also part of pump 388. Bellows 408 is the pump component that draws fluid in through irrigation tube 54 and forces the fluid out through the pump housing 420 and tip assembly 80. The bellows 408, now described with reference to FIGS. 15 and 16 is formed from a flexible thermoplastic and has a cylindrical main body 410 formed with circumferentially extending pleats (not identified). Bellows body 410 has a proximal closed end. A button 414 extends outwardly from the closed end of bellows body 410. A neck 412, that has a diameter less than that of button 414, connects the button to the closed end of the body 410. A lip 416 extends radially outwardly and circumferentially around the open end of bellows body 410.

Upon assembly of the irrigator 50, the neck 412 integral with the bellows is disposed in yoke slot 404. Button 414 is disposed against the proximally directed face of yoke tab 404. Bellows lip 416 is disposed against the distally directed surfaces of one of the webs 258 and the web 300 internal to barrel 92. This component contact prevents proximal movement of the bellows 408. The back and forth reciprocation of the yoke 390 results in a like expansion and contraction of the bellows main body 410.

Pump housing 420 is the component of pump 388 to which irrigation tube 54, suction tube 56 and bellows 408 is connected. The pump housing 420 is also the component internal to handpiece 52 to which the irrigation tube 82 and suction tube 84 of the tip assembly 80 are connected. The pump housing 420 is located in the barrel 94 forward of bellows 408. As seen best in FIGS. 17, 17A and 17B the pump housing 420 is formed from a single piece of molded plastic and includes a base 424. The base 424 includes an outer sleeve 426 that along the outer surface is of generally of constant diameter. A lip 428 protrudes radially outwardly from the proximal end of sleeve 426. A ring 430 extends proximally rearward from lip 428. Ring 430 is located inwardly of the outer perimeter of lip 428. In the depicted version of the invention, ring 430 has an inner diameter that is greater than the outer diameter of outer sleeve 426. Pump housing is further formed so that along the outer surface of the ring a step 432 extends circumferentially around the ring. The outer diameter of the proximal portion of the ring 430 is thus less than the outer diameter to the distal portion of the ring, the portion distal to step 432. Two flexible legs 434 extend rearwardly from lip 428. Legs 434 are diametrically opposed to each other. Each leg 434 is formed with an inwardly directed foot 436.

Pump housing 422 is formed with an inner sleeve 438 that is coaxial with and disposed in outer sleeve 426. Inner sleeve 438 extends distally from the proximal end of the outer sleeve 426. The inner sleeve 438 terminates at a location approximately at the mid plane through the outer sleeve. Not identified is the circular web internal to the outer sleeve that extends to the inner sleeve. Sleeves 426 and 438 are dimensioned that that there is an annular gap between the sleeves (gap not identified). At the proximal end of the inner sleeve 438 a circular lip 442 projects inwardly from the sleeve.

The outer sleeve 426 is further formed so that three bores collectively extend through the sleeve. A first bore, bore 446 is defined by the inner wall of the inner sleeve 438. A second bore, bore 480 is located immediately forward of bore 446. The third bore, bore 482 forms the distal end opening into the outer sleeve 426. The sleeve 426 is formed so that bore 482 has a diameter greater than that of bore 480.

Figure 17B:
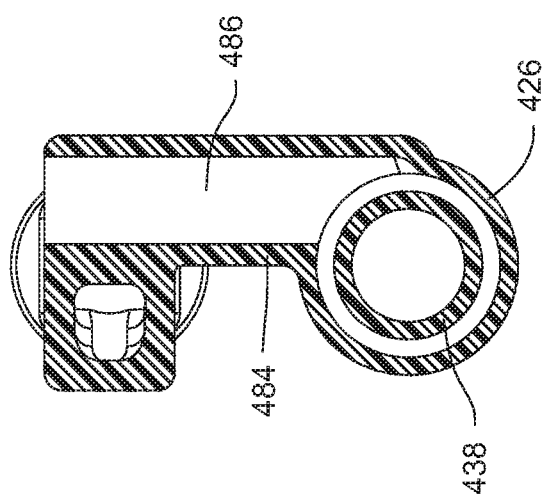
FIGS. 17A and 17B are cross sectional views of the pump housing.
Figure 17A:
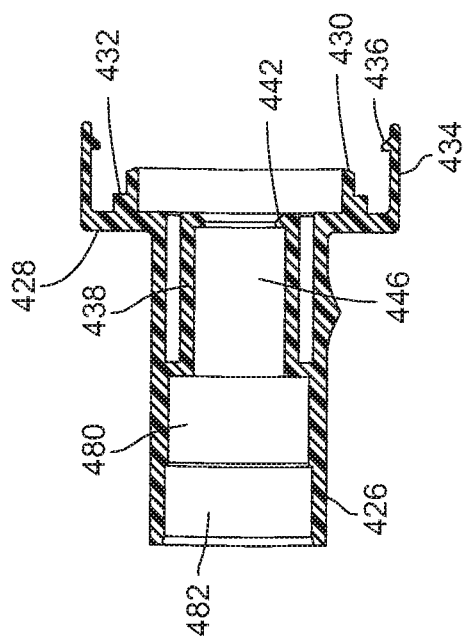

Pump housing 422 is further formed to have a cylindrical neck 484. Neck 484 extends perpendicularly upwardly from outer sleeve 426. The pump housing 484 is formed so that the neck 484 extends upwardly along an axis that, in addition to being perpendicular to the longitudinal axis through sleeve 426 is laterally offset from the longitudinal axis through sleeve 426. Neck 484 is formed with a channel 486. As seen in FIGS. 17A and 17B, channel 486 opens into the annular gap between outer and inner sleeves 426 and 438.

Housing neck 484 extends to a head 490. Pump housing head 490 has a main section, not identified, that is formed from a number of subs-section that can generally be considered polygonal in shape. In the disclosed version of the invention, the head 490 is formed with a top located opening 492. The opening 492 is coaxial with neck channel 486. Opening 492 is present as a result of the injection molding process used to form pump housing 422. More specifically, the opening 492 is present as a result of the component of the mold that defines neck channel 486. During the process of manufacturing handpiece 64 a cap, not depicted, is fitted on the top of housing head 490 to close opening 492.

The pump housing 420 is formed so that two fittings, fittings 496 and 504, extend proximally from the proximally directed face of the head 490. Fitting 496 is the fitting to which the distal end of irrigation tube 54 is fitted. The housing 420 is formed with a closed end bore, not depicted, that extends through fitting 496 partially through the head 490 to the neck channel 486. This bore is the conduit through which the irrigating fluid flows from the irrigation tube into the pump housing base 424.

A cylindrical nose 502 extends distally forward from the housing head 490. Nose 502 is formed with a cylindrical bore 512 that extends proximally rearward from the distal front end of the nose. Nose 502 and bore 512 share a common longitudinal axis. An extension of this axis would extend through the housing head 490 between where the fittings 496 and 504 extend from the head. Channels, not identified, function as the fluid communication path through the head from fitting 502 to bore 512.

Upon assembly of handpiece 52, the pump housing 420 is sandwiched between the barrel right side shell webs 258 and the barrel left side shell webs 300 and 302. The distal end of irrigation tube 54 is attached to fitting 496. The distal end of the suction tube 56 is attached to fitting 504.

A duck billed valve 526, seen in FIGS. 15 and 16, is seated in the bore defined by housing bore 446. Valve 526 is arranged so that the open end of the valve is directed towards the bellows 520. The lips of the valve 526 are directed towards tube bore 480. Valve 526 has a base 528 that extends radially outwardly from the valve around the open end of the valve. Base 528 is curved in cross section. The outer perimeter of the valve base 528 extends over the proximal end of the inner sleeve 438 and the adjacent lip 442. Base 528 thus forms an umbrella-type inlet valve into the bellows. More particularly this inlet valve is located around the outer perimeter of the pump chamber defined by the bellows.

An O-ring 524, seen only in FIG. 15, is seated on the step 432 integral with ring 430. The O-ring 524 is pressed between the housing ring 430 and bellows lip 416. The O-ring 524 contributes to the seal between the bellows 514 and pump housing base 424. The housing legs 434 extend over the outer surfaces of bellows ring 520. The housing feet 436 extend over the bellows lip 416 so as to hold the bellows 408 to the pump housing 424.

An understanding of how an energization signal is selectively applied to motor 340 is obtained by reference to FIGS. 2 and 18. A cable 532 seen as a dashed cylinder in FIG. 18 is typically bundled with the assembly that comprises the paired irrigation tube 56 and suction tube 66. The proximal end of the cable is connected to a power supply 530 associated with the lavage unit 50. This power supply 530 may take the form of a battery pack. Alternatively, the power supply may take the form of a device that converts AC voltage into DC voltages that are two different potentials. The exact structure of the power supply is not a part of the structure of the lavage unit 50 of this application. In FIG. 18 the power supply 530 is depicted as four series connected cells Trigger 534 is pivotally mounted to the right and left side shells posts 117 and 115, respectively, by pins not seen. Also disposed in handgrip shells 102 and 162 is flexible conductive contact 536. The means by which the trigger 534 and contact 536 are mounted in the handgrip is not part of the present invention.

Internal to the cable 532 are a number of insulated wires. One wire, wire 538 extends from the power source to a contact integral with the motor 340 (motor contact not illustrated). A second wire, wire 540 extends from the power supply to contact 536. Internal to the handgrip 92 is a conductive post 542. Post 542 is positioned so that when contact 536 is flexed, the contact will abut the post. Internal to the handpiece handgrip 92 is an insulated wire 544. Wire 544 extends from post 542 to a second terminal of the motor 340.

Normally, trigger 534 is spaced away from contact 536. Contact 536 is spaced away from conductive post 542. The circuit between motor 340 and power supply 530 is thus an open circuit. The pivoting of the trigger 534 causes the trigger to abut and flex contact 536. The flexing of the contact 536 causes the contact to abut conductive post 542. The abutting of the contact 536 against the post functions as a switch that closes the circuit between the motor and the power supply 530.

Tip assembly 80 includes a connector 81 seen best in FIGS. 2 and 3. Connector 81 includes features that cooperate with the barrel openings 306 and indentations 308 to removably hold the tip assembly 80 to the handpiece 52. Connector 81 also includes tubular members (not identified) that seat in pump housing bores 482 and 512. The tubular member that seats in pump housing bore 482 establishes the fluid communications path from the pump housing 422 to the irrigation tube 82 integral with the tip assembly 80. The tubular member that seats in pump housing bore 512 establishes the fluid communications path from the tip assembly suction tube to the pump housing 422.

II. Operation

Lavage unit 50 of this invention is prepared for use by attaching the tip assembly 80 to the handpiece 52. Irrigation tube 54 is connected to a source of irrigating fluid 53. Suction tube 56 is connected to container 58 and suction source 60. If necessary cable 352 is connected to a power supply. Once these steps are complete, the lavage unit is ready for operation.

The lavage unit 50 is operated by the depression of trigger 534. The resultant abutment of contact 536 against conductive post 542 results in the flow of an energization signal, energization current, to motor 340. The resultant actuation of the motor 340 causes the reciprocation of bellows 408. During the phase of a cycle in which the bellows is retracted, irrigation fluid is drawn into the bellows from the irrigation tube 54. During the phase of cycle in which the bellows is compressed, the irrigation fluid is discharged through the pump housing 420 and out through the tip assembly irrigation tube 86.

By depressing lock button 320 at any time the angular orientation of the handpiece barrel 94 relative to the handgrip 92 can be selectively set. This is referred to as transferring the lock assembly from the set state to the adjust state. Thus, the practitioner can operate the handpiece as a pistol type unit as depicted in FIG. 1, as a wand type unit as seen in FIG. 19 or in an intermediate shape between these two configurations. Regardless of the angular orientation of the barrel 94, the eccentric gear 368 remains at a fixed position relative to face gear 348 and yoke 390. This ensures that regardless of the orientation of the barrel 94 the motor 340 is still able to actuate the pump.

Thus, lavage unit 50 of this invention can be operated in a configuration that is most ergonomically comfortable for the specific procedure being performed. While not always the case, if the tissue against which the unit 50 is to be applied is waist high or lower to the practitioner, the unit is operated in the pistol configuration. If the tissue to which the unit is applied is above the waist of the practitioner, many practitioners find it useful to operate the unit in something closer to the wand configuration.

When operating the lavage unit 50 in the wand configuration, it should be understood that the practitioner is of course free to hold the handpiece 52 by the handgrip 92, the barrel 94, the joint 310 or any combination of these components. When the handpiece is so held, the practitioner will often use the thumb or forefinger to depress the trigger 534.

Handpiece 52 of this invention is further designed so that both the irrigation tube 54 and suction tube 56 are disposed in the handgrip 92 and barrel 94. Thus, regardless of the orientation of the barrel 94 to the handgrip 92, these tubes are not loose components that interfere with the handling of the lavage unit. 50. In response to the pivoting of the barrel, the irrigation tube 54 and suction tube 56 flex around the outer surface of the joint. The portions of these tubes 54 and 56 disposed within the barrel remain static. Thus even if the barrel 94 is repeatedly pivoted during a procedure, there is essentially no possibility that the tubes 54 and 56 will work lose from the pump housing 420.

Another feature of the lavage unit of this invention is that the handgrip ear 122 and 166 and barrel feet 222 and 264 close off the interior of the joint between the handgrip 92 and barrel 94. There is essentially no likelihood that an article of clothing, a stray medical device or a curious finger could become caught in this joint.

III. First Alternative Pump

Figure 21:
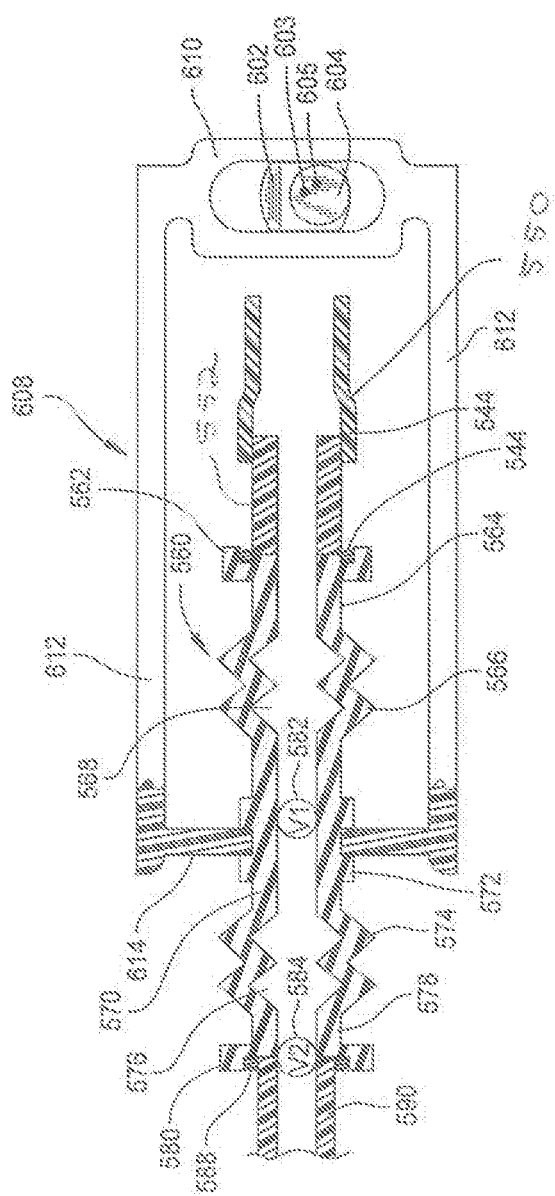
FIG. 21 is depicts an alternative pump of that can be employed in a handpiece.
Figure 22:
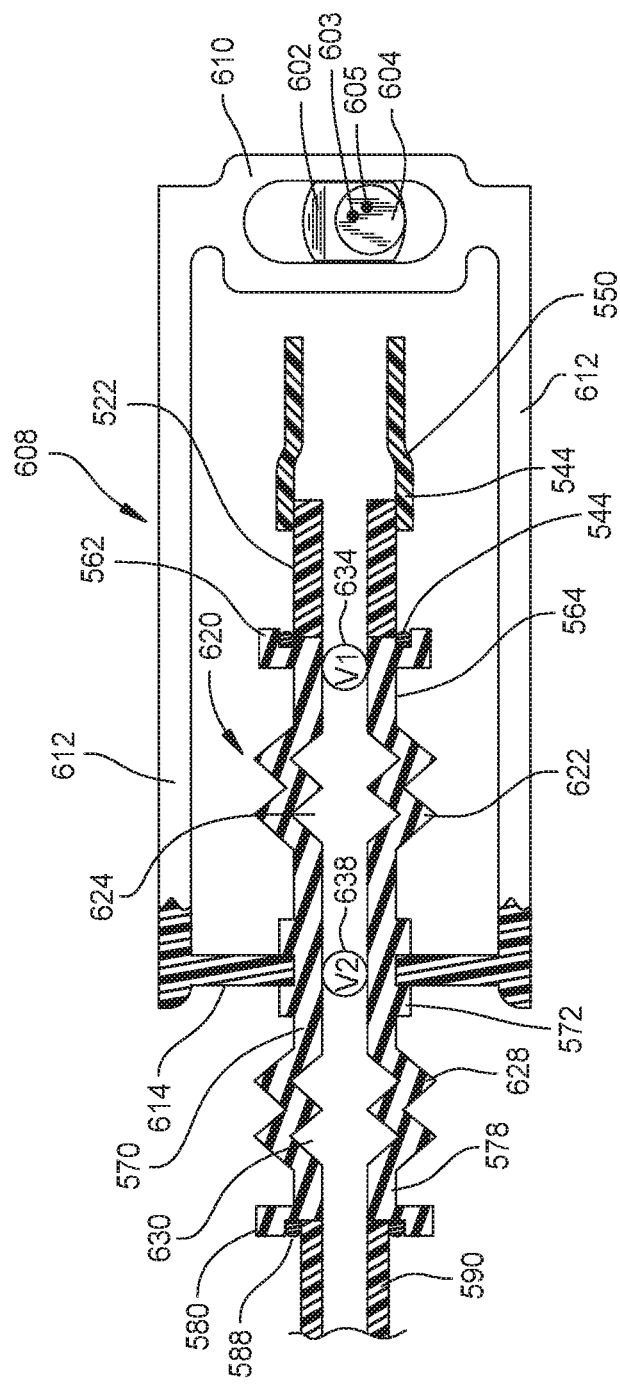
FIG. 22 is depicts a second alternative pump of that can be employed in a handpiece.

An alternative bellows 560 that can be incorporated into a lavage unit, including the lavage unit with the pivotable handpiece 52 described above is now described by reference to FIG. 21. Bellows 560 receives irrigation fluid from an irrigation tube 550 similar to tube 54. The distal end of tube 550 is attached to a tube shaped inlet fitting 552. This inlet fitting 552, identified in FIG. 22, is typically statically mounted in the handpiece in which bellows 560 is installed. Inlet fitting 552 leads into the proximal end of the bellows 560.

The bellows 560 itself extends between the inlet fitting 542 and rigid outlet fitting 590. Outlet fitting 590 is analogous to sleeve 426, lip 428, ring 430 and legs 434 of the previously described pump housing 420. Bellows 560 is formed from flexible material. This material may be rubber, thermoplastic, polyethylene or polypropylene. At the proximal end, the bellows has a foot 562, that, in cross section, is L-shaped. Foot 562 is shaped to fit over the open distal end of the inlet fitting 542. An O-ring 544 disposed around the perimeter of the inlet fitting 542, provides a seal between the fitting and lip 562. Extending forward from foot 562, bellows 560 has a leg 564 that is generally tubular in shape. Forward of leg 564, the bellows has a proximal pleated section 566. Proximal pleated section 566 thus defines a supplemental chamber, a supply chamber 568, internal to the bellows 560. A tubular torso 570 is located forward of the proximal pleated section 566. Torso 570 is formed to have around the outer surface two spaced apart ribs 572, only one identified. Ribs 572 extend partially, if not fully, circumferentially around the torso 570.

Torso 570 opens into a distal pleated section 574. The distal pleated section 574 defines a pump chamber 576. A tubular head 578 extends forward from the distal pleated section 574. A lip 580 extends forward and outwardly around the open end of head 578. The lip 580, which is L-shaped in cross section, extends around the open proximal end of the outlet fitting 590. An O-ring 588 disposed around the outer proximal end of the outlet fitting 590 provides a seal between the bellows 560 and the fitting.

Internal to the bellows is a proximal valve 582. Valve 582 is a one-way valve that only allows flows in the valve from the proximal end of the bellows to and through the distal end. The proximal valve is located in the torso 570 so as to be between chambers 568 and 576. Valve 582 is thus the inlet valve into the pump chamber 576. The proximal valve 582 may be a duck bill valve, an umbrella valve or a flapper valve. The lavage unit of this invention also has a distal valve 584. Distal valve may be located wholly or partially end bellows head 578 or the adjacent section of the outlet fitting 590. Distal valve 584 is a one way valve that only allows flow in the same direction in which the proximal valve 582 allows flow. Distal valve 584 may have the same structure of one of the above-described valves that form the proximal valve 582. Distal valve 584 is thus functions as the outlet valve from the pump chamber 576.

While not illustrated, portions of either valve 582 or 584 may be molded integrally with the bellows 560. Alternatively, the bellows 560 may have molded internal features, such as ribs, that facilitate the mounting of one or more of the valves 582 or 584 to the bellows. Also, in the illustrated version of the invention, the wall thickness of the bellows is shown as constant along the length of the bellows. This is for ease of illustration only. In versions of the invention in which the bellows is molded as a single piece unit, the sections of the bellows that defines the supplemental (supply) chamber 568 and the pump chamber 576 often have a reduced wall thickness. Thus. pleated sections 566 and 574 often have a wall thickness less than that of leg 564, torso 570 and head 578.

An eccentric gear 602 and yoke 608 reciprocate the bellows 560. The eccentric gear 602 (teeth not shown) is similar to the previously described eccentric gear 368. Not shown is the drive assembly that rotates the eccentric gear. This assembly could be the previously described motor 340 and face gear 348. Eccentric gear 602 has a cylindrical head 604. The eccentric gear 602 is constructed so that head 604 is centered on an axis, identified by point 605, that is offset from the axis, identified by point 603, around which the eccentric gear rotates.

Yoke 608 includes a generally rectangular frame 610. The center of the frame 610 is open. More particularly the void space internal to the frame has a lateral dimension that allows the slip fitting of eccentric gear head 604 in the space. The length along the longitudinal axis of the void space is greater than the diameter of the eccentric gear head. Two legs 612 extend distally forward from the opposed side ends of the frame 610. A foot 614, only one identified, extends inwardly from each leg 612 adjacent the distal end of the leg. Feet 614 extend between the ribs 572 located around the outer surface of bellows 560. The yoke is mounted to the handpiece in which it is installed so that it will reciprocate back and forth along the axis parallel to legs 612.

An irrigation unit that includes bellows 560 is used like a conventional irrigation unit. The unit is actuated by energizing the motor internal to the unit handpiece. The energization of the handpiece results in the rotation of the eccentric gear 602. Rotation of the eccentric gear results in the reciprocation of the yoke 608.

Figure 21A:
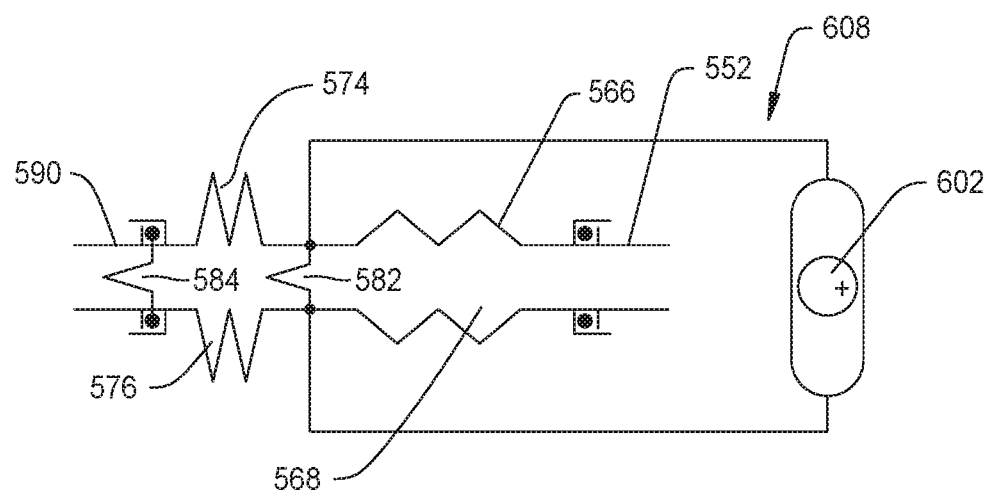
FIGS. 21A and 21B are diagrammatic depictions of the state of the pump of FIG. 21 when the pump is in two different phases that occur during the cycling of the pump.

As a result of the reciprocation of the yoke, the bellows pleated sections 566 and 574 are cyclically expanded and compressed. A first phase, seen in FIG. 21A, can be considered the departure from the position of the state of the bellows in FIG. 21 in which the yoke legs 612 move distally forward. This movement results in the compression of the bellows distal pleated section 574. Pump chamber 576 is forced to its minimal volume. Owing to the presence of valves 582 and 584 any fluid in the chamber 576 is forced out of chamber 576 through the outlet valve 584 and the outlet fitting 590 and the tip assembly 80 attached to the handpiece.

Figure 21B:
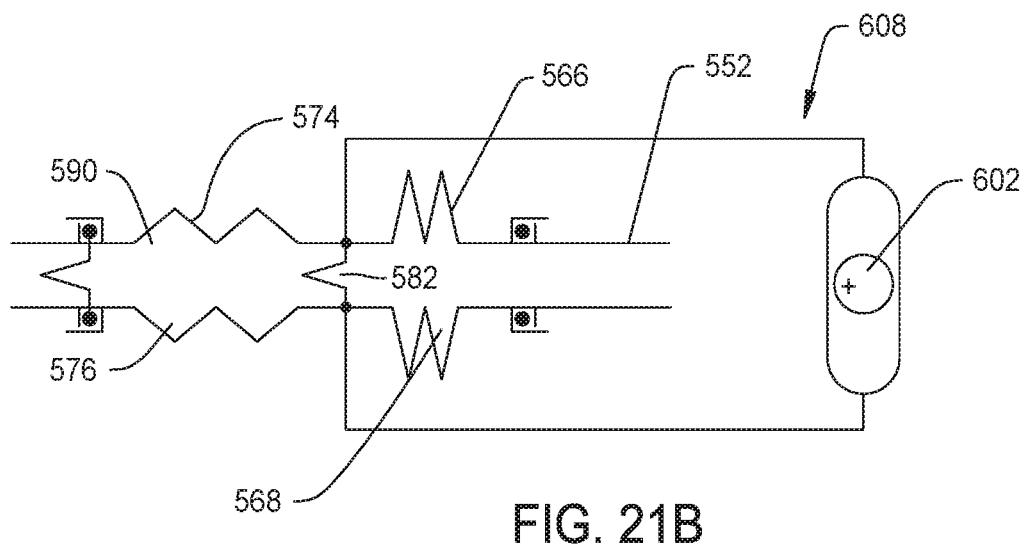

The next phase in the cycle is the movement of the yoke from the distally extended state to the proximal retracted state. During initial part of this phase, the volume of the supply chamber 568 increases. The pressure in the supply chamber 568 thus falls relative to the upstream pressure in the irrigation supply tube 550 and inlet fitting 552. This pressure drop causes the fluid in the tube 550 and fitting 552 to flow into the supply chamber 568. As a result of the continued movement of the yoke 608, the proximal pleated section is compressed as seen in FIG. 21B. The volume of the supply chamber the 568 falls to the minimal volume. Also at this time valve 584 prevents backflow of fluid from the outlet fitting 590 into the pump chamber 576. Thus during the movement of the bellows 560, fluid in the supply chamber 568 flows past valve 582 into the pump chamber 576. After the movement of the bellows 560 from the state in which the proximal pleated section 566 is compressed, yoke 608 reciprocates the bellows back to the state depicted in FIG. 21A.

It should be understood that the reciprocation of the yoke 608, in addition to causing the compression/expansion of chambers 568 and 576 causes the reciprocation of valve 582.

An advantage of the pump of the lavage unit of this invention is that the fluid flow from the irrigation supply tube 540 out through the outlet fitting 590 is along a generally proximal-to-distal linear path. The fluid is not required to flow through bent conduits. This invention eliminates the frictional fluid flow loss that results from the fluid having to undergo curved path of travel.

IV. Second Alternative Pump

FIG. 22 depicts a second alternative pump, pump 620, of this invention. Pump 620 has the same bellows like structure of pump 560. Thus, the leg 564, torso 570, head 578 and related components will not be described again. Like pump 560, pump leg 564 is coupled by fitting 552 to irrigation tube 550. Pump head 578 is coupled to outlet fitting 590.

Pump 620 has, between leg 564 and torso 570 a proximal section, section 622, that is pleated or otherwise compressible. Proximal section 622 defines the pump chamber 624 of pump 620. Between torso 570 and head 578, pump 620 has a distal section, section 628, that is pleated or otherwise compressible. Distal section 628 defines a supplemental chamber of pump 620, specifically an outlet chamber 630.

An inlet valve 634 is located between the irrigation tube and pump proximal section 622. An outlet valve 638 is located between the proximal and distal sections 622 and 628, respectively. Outlet valve 638 is located between the outlet from pump chamber 624 and the inlet to the outlet chamber 630.

Eccentric gear 602 and yoke 608 reciprocate bellows 620 in the same general manner in which bellows 560 is reciprocated. During the reciprocation of bellows 560, valve 638 reciprocates with the yoke 608. During a first phase of reciprocation cycle, yoke 608 moves towards eccentric gear 608. This results in the compression of the pump section 622 forming pump chamber 624. Inlet valve 634 prevents backflow of the fluid in the pump chamber 624 back towards the inlet tube 550. Fluid instead flows through outlet valve 638 into the outlet chamber 630.

In the second phase of bellows reciprocation, the yoke 608 moves towards the outlet fitting 590. This results in the compression of the bellows section forming the outlet chamber 630. Valve 638 prevents backflow of fluid in the outlet chamber 630 into the pump chamber 624. Fluid is thus forced from out of the outlet chamber through the outlet fitting and into the tip assemble.

As the yoke 608 moves from the extended position legs 614 away from the eccentric gear 602 to the retracted position, legs close to the eccentric gear, bellows proximal section 622 and pump chamber 624 expand. Owing to the previous compression of section 622, the pump chamber is essentially empty of liquid-state fluid. The volumetric expansion of the pump chamber 624 thus results in the pressure within the chamber falling to a low level relative to the pressure within the inlet fitting 522. This pressure differential is sufficient to cause the irrigating fluid within the inlet fitting 552 to open valve 634 and flow into the pump chamber 624.

V. Alternative Embodiments

The above is directed to two versions of the lavage unit of this invention. Alternative lavage units of this invention may have other features than what has been described.

For example, there is no requirement that all lavage units of this invention with the pivotable barrel 94 have the describe bellows with tandem pump chambers 568 and 576. Likewise, there is no requirement that all versions of the invention with the pump chamber and tandem supplemental chamber have the pivoting barrel 94.

Likewise there is no requirement that all versions of the invention with the pivoting barrel have the pulse type pump described above. In an alternative version of the invention, it may be desirable to provide the lavage unit with another type of pump such as a vane pump or an impeller pump.

Further while it is desirable to design the lavage unit 50 so that the pump motor is in the handgrip 92 and the pump unit is in the barrel 94 this is not required in all versions of the invention. Likewise, this invention is not limited to lavage units with electrically driven motors. Alternative lavage units of this invention may have pneumatic or hydraulic units that provide the mechanical energy for actuating the pump.

Further there is no requirement that the specific gear mounted to the handpiece to rotate around the pivot axis be the eccentric gear 368. In an alternative version of the invention, the face gear 348 so mounted. Generally though one gear that transfers mechanical power from the handgrip-mounted motor to the barrel mounted pump is mounted to the handpiece to rotate around the pivot axis.

Also, in some versions of the invention, the pump unit may be remote from the handpiece. In these versions of the invention the irrigation line and, if provided, the suction line, will still extend through the barrel and through at least a portion of the handgrip.

Similarly, some lavage units of this invention may not include components for drawing a suction away from the site to which the irrigating fluid is applied. In these versions of the invention, the handpiece will not include a suction line.

Alternative means than the disclosed lock button may be incorporated into this invention to releasably hold the barrel 94 in the fixed angular orientation relative to the handgrip. For example the handgrip 92 and barrel 94 may be collectively assembled so that friction contact between these components holds them in a fixed orientation relative to each other. An advantage of this construction of the invention is that it eliminates the need to provide the disclosed lock button and spring. Alternatively, a releasable clamp may releasably hold the barrel 94 in the fixed angular orientation relative to the handgrip 92. When the clamp is in adjust state, the barrel can be freely pivoted. When the clamp is in a lock state, one clamp component presses against another clamp component to prevent the pivoting of the barrel 92 relative to the handgrip 94. An advantage of this version of the invention is that it allows fine setting of the angular orientation of the barrel 94.

The means by which the shells forming the body of the handpiece together is not limited to press fit posts. Snap fit components, fasteners or adhesives can be used to hold these body forming components together.

Further, while it is desirable that the irrigation tube 54 and, if present suction tube 56, extend out the proximal end of the handgrip 92, this is not required. In some version of the invention, these tubes may extend out of the handgrip 92 at a location distal to the proximal end of the grip. Likewise, in some versions of the invention, the irrigation and suction tubes may not even extend fully through the barrel 94. Likewise, in some versions of the invention the tube or tubes that extend between the barrel and grip may be disposed within the joint as opposed to being seated over the joint. A possible advantage of this version of the invention is that it prevents curious fingers from disconnecting the tube or tubes.

Similarly there is no requirement that in all versions of the invention that, when the barrel is pivoted that the irrigation and suction tubes flex. In some versions of the invention separate irrigation and suction tubes may be located in the barrel and handpiece. A bellows serves as the flexing connecting component between the tubes forming each pair of tubes. Also, in some versions of the invention, the tubes may be fitted into the handpiece so that, as a result of the pivoting of the barrel, the sections of the tubes disposed in the handgrip undergo some movement. In some versions of the invention the tubes may both undergo some flexing in combination with, within the handpiece, some movement.

Likewise, it may be desirable in some versions of the invention to mount the trigger assembly or other switch assembly that controls the actuation of the unit to the barrel. In some versions of the invention, it may be desirable to provide the handpiece 52 with two or more triggers or other manually actuated switches. These switches would be located at different positions on the handpiece. Each switch would control the open/closed state of one of a number of parallel conductive paths associated with the control circuit. A benefit of this version of the invention is that when the practitioner wants to hold the handpiece in a manner that may seem unusual there may will be a trigger or switch for actuating the unit near where the handpiece is being held. This eliminates the need for the practitioner to have to position his/her fingers and thumb in an unusually position in order to both hold the handpiece as desired and actuate the lavage unit.

In some versions of the invention, the tip assembly may be integral with the handpiece.

Further in versions of the invention that include the pump with the tandem chambers 568 and 576, the bellows may not always be formed as a single piece unit. The material from which the chambers defining sections of the bellows are formed may even be different from each other.

Also while not described, it should be understood that the actuator of the irrigator of this invention may have some means for regulating the characteristics of the energization signal applied to the motor 340. This allows the practitioner to, in addition controlling the on/off state of the irrigator regulate the flow rate at which the irrigation fluid is discharged.

Accordingly, it is the object of the appended claims to cover all such modifications and variations that come within the true spirit and scope of this invention.

What is claimed is:

1. A lavage unit comprising:
   a handpiece;
   an irrigation tube that extends from a source of irrigating fluid to the handpiece;
   a pump disposed in the handpiece to which the irrigation tube is connected, the pump including a bellows, the bellows having a section that defines a pump chamber and an outlet, the bellows configured so that, when the bellows is reciprocated, the bellows draws fluid from the irrigation tube into the pump chamber and then discharges the fluid out of the pump chamber through the outlet;
   an inlet valve that allows fluid flow into the pump chamber from the irrigation tube and that blocks fluid flow from the pump chamber towards the irrigation tube;
   an outlet valve that allows fluid flow from the pump chamber into the outlet and that blocks fluid flow from the outlet into the pump chamber;
   a motor and a linkage disposed in the handpiece for reciprocating the bellows; and
   wherein the pump further includes a section of the bellows formed from compressible or flexible material that defines a supplemental chamber that is located between the pump chamber and the pump outlet;
   wherein the outlet valve is located between the pump chamber and the supplemental chamber and the inlet valve is located between the irrigation tube and the supplemental chamber; and
   wherein the linkage is connected to said pump so as to alternatingly compress the bellows forming the pump chamber and the section forming the supplemental chamber, and so that during the movement of the linkage, the outlet valve that is located between the pump chamber and the supplemental chamber reciprocates with the linkage.

2. The lavage unit of claim 1, wherein the irrigation tube, the bellows, and the outlet are arranged in the handpiece so that a distal end of the irrigation tube, the bellows, and the outlet are substantially linearly aligned.

3. The lavage unit of claim 1, wherein the bellows, including the section that defines the pump chamber and the section that defines the supplemental chamber, is a single piece unit.

4. The lavage unit of claim 1, wherein the bellows of the pump is formed from flexible material and/or pleats; and
   wherein the section of the pump forming the supplemental chamber is formed from flexible material and/or pleats.

5. The lavage unit of claim 1, wherein the handpiece further comprises a proximally located handgrip and a distally located barrel; and
   wherein the pump is disposed in the barrel of the handpiece, the motor is disposed in the handgrip of the handpiece, and the linkage is disposed in the barrel of the handpiece.

6. The lavage unit of claim 1, further comprising at least one manually actuatable member mounted to the handpiece for regulating the discharge of irrigating fluid from the handpiece.

7. The lavage unit of claim 1, wherein a suction tube that extends to a suction source extends through the handpiece.

8. The lavage unit of claim 1, further comprising a tip assembly that is removably coupled to the handpiece; and
   wherein the tip assembly extends forward from the handpiece, the tip assembly including an irrigation tube that receives the fluid discharged from the pump outlet for discharge towards the tissue to which the lavage unit is applied.

9. The lavage unit of claim 8, wherein the handpiece includes a distally located barrel from which the tip assembly extends and a handgrip that extends proximally from the barrel that is fixedly attached to the barrel.

10. The lavage unit of claim 1, further comprising a tip assembly that is removably coupled to the handpiece, the tip assembly comprising:
    a tip assembly irrigation tube having spaced apart proximal and distal ends wherein the tip irrigation tube receives the fluid discharged from the outlet and the fluid is discharged from the tip assembly irrigation tube through the distal end of the tip assembly irrigation tube; and
    a connector associated attached to the tip assembly irrigation tube that has features for holding the tip assembly irrigation tube to the handpiece of the lavage unit.

11. The lavage unit of claim 10, further comprising a suction tube through which a suction can be drawn from a site to which the distal end of the tip assembly irrigation tube is applied.

12. The lavage unit of claim 11, wherein the tip assembly irrigation tube is disposed inside the suction tube.

13. The lavage unit of claim 10, further comprising a spray shield removably attached over the tip assembly irrigation tube.

14. A lavage unit comprising:

a handpiece;

an irrigation tube that extends from a source of irrigating fluid to the handpiece;

a pump disposed in the handpiece to which the irrigation tube is connected, the pump including a bellows comprising:
- a proximal section defining a pump chamber and an inlet; and
- a distal section defining a supplemental chamber and an outlet;

an inlet valve that allows fluid flow into the pump chamber and blocks fluid flow from the pump chamber towards the irrigation tube;

an outlet valve that allows fluid flow from the pump chamber into the supplemental chamber and blocks fluid flow from the supplemental chamber into the pump chamber;

a linkage disposed in the handpiece for reciprocating the bellows; and wherein the proximal section is configured so that, when the proximal section is reciprocated, the proximal section draws fluid from the irrigation tube into the pump chamber through the inlet and then discharges the fluid to the supplemental chamber;

wherein the distal section is configured so that, when the distal section is reciprocated, the distal section receives fluid from the pump chamber into the supplemental chamber and then discharges the fluid out of the supplemental chamber through the outlet;

wherein the outlet valve is located between the pump chamber and the supplemental chamber; and wherein the linkage is connected to the pump so as to alternatingly compress the distal section forming the supplemental chamber and the proximal section forming the pump chamber, and so that during the movement of the linkage, the outlet valve that is located between the supplemental chamber and the pump chamber reciprocates with the linkage.

15. The lavage unit of claim 14, further comprising:

a tip assembly that extends forward from the handpiece, the tip assembly including an irrigation tube that receives the fluid discharged from the pump outlet for discharge towards the tissue to which the lavage unit is applied; and a suction tube through which a suction can be drawn from a site to which the distal end of the irrigation tube is applied.

16. A lavage unit comprising:

a handpiece;

an irrigation tube that extends from a source of irrigating fluid to the handpiece;

a pump disposed in the handpiece to which the irrigation tube is connected, the pump including a bellows, the bellows having a section that defines a pump chamber and an outlet, the bellows configured so that, when the bellows is reciprocated, the bellows draws fluid from the irrigation tube into the pump chamber and then discharges the fluid out of the pump chamber through the outlet;

an inlet valve that allows fluid flow into the pump chamber from the irrigation tube and that blocks fluid flow from the pump chamber towards the irrigation tube;

an outlet valve that allows fluid flow from the pump chamber into the outlet and that blocks fluid flow from the outlet into the pump chamber;

a motor and a linkage disposed in the handpiece for reciprocating the bellows; and a tip assembly that is removably coupled to the handpiece, the tip assembly comprising:
- a tip assembly irrigation tube having spaced apart proximal and distal ends wherein the tip assembly irrigation tube receives the fluid discharged from the outlet and the fluid is discharged from the tip assembly irrigation tube through the distal end of the tip assembly irrigation tube; and
- a connector associated attached to the tip assembly irrigation tube that has features for holding the tip assembly irrigation tube to the handpiece of the lavage unit; and a suction tube through which a suction can be drawn from a site to which the distal end of the tip assembly irrigation tube is applied, the tip assembly irrigation tube being disposed inside the suction tube;

wherein the pump further includes a section of the bellows formed from compressible or flexible material that defines a supplemental chamber that is either located between the irrigation tube and the pump chamber or between the pump chamber and the pump outlet;

wherein, when the supplemental chamber is located between the irrigation tube and the pump chamber, the inlet valve is located between the supplemental chamber and the pump chamber;

wherein, when the supplemental chamber is located between the pump chamber and the pump outlet, the outlet valve is located between the pump chamber and the supplemental chamber; and wherein the linkage is connected to said pump so as to alternatingly compress the bellows forming the pump chamber and the section forming the supplemental chamber, and so that during the movement of the linkage, whichever of the inlet valve or the outlet valve that is located between the pump chamber and the supplemental chamber reciprocates with the linkage.

17. The lavage unit of claim 16, wherein, when the supplemental chamber of the pump is located between the irrigation tube and the pump chamber, the outlet valve is located between the pump chamber and the outlet.

18. The lavage unit of claim 16, wherein, when the supplemental chamber is located between the pump chamber and the pump outlet, the inlet valve is located between the irrigation tube and the supplemental chamber.

19. The lavage unit of claim 16, wherein the handpiece further comprises a proximally located handgrip and a distally located barrel; and wherein the pump is disposed in the barrel of the handpiece, the motor is disposed in the handgrip of the handpiece, and the linkage is disposed in the barrel of the handpiece.

* * * * *